(12) United States Patent
Dowds et al.

(10) Patent No.: US 10,872,681 B2
(45) Date of Patent: *Dec. 22, 2020

(54) DIFFERENTIAL FILTERING OF GENETIC DATA

(71) Applicant: Affymetrix, Inc., Carlsbad, CA (US)

(72) Inventors: Carl A. Dowds, Sunnyvale, CA (US); Jody C. McIntyre, Pacifica, CA (US); Edgar E. Erwin, Berkeley, CA (US); Garret D. Wilson, San Francisco, CA (US); Pragna B. Parmar, Cupertino, CA (US); Breck S. Ohlson, Gilroy, CA (US); Richard D. Shippy, Scottsdale, AZ (US); Francisco J. Cifuentes, San Francisco, CA (US)

(73) Assignee: Affymetrix, Inc., Carlsbad, CA (US)

( * ) Notice: Subject to any disclaimer, the term of this patent is extended or adjusted under 35 U.S.C. 154(b) by 594 days.

This patent is subject to a terminal disclaimer.

(21) Appl. No.: 15/713,556

(22) Filed: Sep. 22, 2017

(65) Prior Publication Data

US 2018/0011970 A1 Jan. 11, 2018

Related U.S. Application Data

(63) Continuation of application No. 12/986,986, filed on Jan. 7, 2011, now Pat. No. 9,798,855.

(Continued)

(51) Int. Cl.
*G16B 45/00* (2019.01)
*G16B 20/00* (2019.01)
*G16B 25/00* (2019.01)

(52) U.S. Cl.
CPC ............. *G16B 45/00* (2019.02); *G16B 20/00* (2019.02); *G16B 25/00* (2019.02)

(58) Field of Classification Search
CPC ............ C12Q 2600/156; C12Q 1/6809; C12Q 2537/16; C12Q 1/6874; C12Q 2537/165;
(Continued)

(56) References Cited

U.S. PATENT DOCUMENTS 5,593,839 A 1/1997 Hubbell et al.
5,733,729 A 3/1998 Lipshutz et al.
(Continued)

OTHER PUBLICATIONS

Wang et al., "Large-Scale Identification, Mapping and Genotyping of Single-Nucleotide Polymorphisms in the Human Genome," Science, vol. 280, May 15, 1998, pp. 077-1082.
(Continued)

*Primary Examiner* — Mary K Zeman
(74) *Attorney, Agent, or Firm* — Mauriel Kapouytian Woods LLP; Elaine K. Lee; Michael Mauriel

(57) ABSTRACT

Computer software products, methods, and systems are described which provide functionality to a user conducting experiments designed to detect and/or identify genetic sequences and other characteristics of a genetic sample, such as, for instance, gene copy number and aberrations thereof. The presently described software allows the user to interact with a graphical user interface which depicts the genetic information obtained from the experiment. The presently disclosed methods and software are related to bioinformatics and biological data analysis. Specifically, provided are methods, computer software products and systems for analyzing and visually depicting genotyping data on a screen or other visual projection. The presently disclosed methods and software allow the user conducting the experiment to differentially filter complex genetic data and information by varying genetic parameters and removing or highlighting visually various regions of genetic data of interest (CytoRegions). These differential filters may be applied by the user
(Continued)

to the entire set of genetic data and/or only to the specific CytoRegions of interest.

20 Claims, 9 Drawing Sheets

Related U.S. Application Data

(60) Provisional application No. 61/292,930, filed on Jan. 7, 2010.

(58) Field of Classification Search
CPC ........ C12Q 1/68; C12Q 1/6813; C12Q 1/682; G16B 20/00; G16B 40/00; G16B 25/00; G16B 30/00; G16B 20/10; G16B 40/20; G16B 40/30; G16B 25/10; G16B 5/00; G16B 99/00; G16B 10/00; G16B 20/20; G16B 30/20; G16B 15/00; G16B 25/20; G16B 30/10; G16B 35/00; G16B 45/00; G16B 50/00; G16B 5/20; G16H 50/20; G16H 10/40; G16H 50/30; G16H 20/10; G16H 10/20; G16H 10/60; G16H 15/00; G16H 40/63; G16H 50/50; G16H 50/70; G16H 70/60; G06N 7/005; G06N 20/00; G06N 20/10; G06N 20/20; G06N 5/003; G06F 19/00; G06F 17/18; G06F 16/9024; G06F 19/18; G06F 19/20
See application file for complete search history.

(56) References Cited

U.S. PATENT DOCUMENTS

| | | | |
|---|---|---|---|
| 5,795,716 A | 8/1998 | Chee | |
| 5,858,659 A | 1/1999 | Sapolsky et al. | |
| 5,974,164 A | 10/1999 | Chee | |
| 6,066,454 A | 5/2000 | Lipshutz et al. | |
| 6,090,555 A | 7/2000 | Fiekowsky et al. | |
| 6,185,561 B1 | 2/2001 | Balaban et al. | |
| 6,188,783 B1 | 2/2001 | Balaban et al. | |
| 6,223,127 B1 | 4/2001 | Berno | |
| 6,308,170 B1 | 10/2001 | Balaban | |
| 6,420,108 B2 | 7/2002 | Mack et al. | |
| 6,611,767 B1 | 8/2003 | Fiekowsky et al. | |
| 6,687,692 B1 | 2/2004 | Balaban et al. | |
| 6,816,867 B2 | 11/2004 | Jevons et al. | |
| 6,829,376 B2 | 12/2004 | Bartell | |
| 6,954,699 B2 | 10/2005 | Jevons et al. | |
| 7,031,846 B2 | 4/2006 | Kaushikkar et al. | |
| 7,130,458 B2 | 10/2006 | Bartell | |
| 7,280,922 B2 | 10/2007 | Mei et al. | |
| 7,451,047 B2 | 11/2008 | Jevons et al. | |
| 7,992,098 B2 | 8/2011 | Kaushikkar et al. | |
| 8,027,823 B2 | 9/2011 | Barrett et al. | |
| 8,392,355 B2 | 3/2013 | Kennedy et al. | |
| 8,855,935 B2 | 10/2014 | Myres et al. | |
| 9,798,855 B2 * | 10/2017 | Dowds ................. | G16B 45/00 |
| 2002/0183936 A1 | 12/2002 | Kulp et al. | |
| 2003/0100995 A1 | 5/2003 | Loraine et al. | |
| 2003/0157545 A1 | 8/2003 | Jevons et al. | |
| 2004/0006431 A1 | 1/2004 | Bartell et al. | |
| 2004/0126840 A1 | 7/2004 | Cheng et al. | |
| 2004/0138821 A1 | 7/2004 | Chiles et al. | |
| 2004/0199544 A1 | 10/2004 | Balaban et al. | |
| 2004/0220897 A1 | 11/2004 | Bernhart et al. | |
| 2005/0123971 A1 | 6/2005 | Di et al. | |
| 2005/0287575 A1 | 12/2005 | Di et al. | |
| 2006/0142949 A1 | 6/2006 | Helt | |
| 2006/0184038 A1 | 8/2006 | Smith et al. | |
| 2006/0241868 A1 | 10/2006 | Sun et al. | |
| 2008/0287308 A1 | 11/2008 | Hubbell et al. | |
| 2009/0098547 A1 | 4/2009 | Ghosh | |
| 2009/0137417 A1 * | 5/2009 | Fu ........................ | C12Q 1/6837 506/9 |
| 2010/0281401 A1 * | 11/2010 | Tebbs ...................... | G06F 19/00 715/760 |
| 2011/0250602 A1 | 10/2011 | Rosenow et al. | |
| 2012/0214704 A1 | 8/2012 | Huang et al. | |
| 2013/0169645 A1 | 7/2013 | Mack et al. | |

OTHER PUBLICATIONS

Gingeras, et al., "Simultaneous Genotyping and Species Identification Using Hybridization Pattern Recognition Analysis of Generic *Mycobacterium* DNA Arrays," Genome Research, 8, Feb. 17, 1998, pp. 435-448.

Halushka, et al., "Patterns of single-nucleotide polymorphisms in candidate genes for blood-pressure homeostasis," Nature Genetics, vol. 22, Jul. 1999, pp. 239-247.

Eddy, Sean R., "What is a hidden Markov model?," Nature Biotechnology, vol. 22, No. 10, Oct. 2004, pp. 1315-1316.

Rabiner, L., "A Tutorial on Hidden Markov Models and Selected Applications in Speech Recognition," Proceedings of the IEEE, vol. 77, Feb. 1989, pp. 257-286.

Mei et al., "Genome-wide Detection of Allelic Imbalance Using Human SNPs and High-density DNA Arrays," Genome Research, Jun. 10, 2000, pp. 1126-1137.

Lindblad-Toh et al., "Loss-of-heterozygosity analysis of small-cell lung carcinomas using single-nucleotide polymorphism arrays," Nature Biotechnology, vol. 18, Sep. 2000, pp. 1001-1005.

Parks et al., "GenGIS: A geospatial information systems for genomic data," Genome Research, vol. 19, 2009, pp. 1896-1904.

* cited by examiner

DIFFERENTIAL FILTERING OF GENETIC DATA

CROSS REFERENCE TO RELATED APPLICATIONS

This application is a continuation of U.S. application Ser. No. 12/986,986 filed Jan. 7, 2011, which claims priority to U.S. Provisional Application No. 61/292,930 filed Jan. 7, 2010. The entire contents of these applications are hereby incorporated herein by reference.

FIELD OF THE INVENTION

The presently disclosed methods and software are related to bioinformatics and biological data analysis. Specifically, provided are methods, computer software products and systems for analyzing and displaying to a user, genetic data and genetic information obtained from a genetic sample. The systems include a processor and a memory coupled with the processor, the memory storing a plurality of machine instructions that cause the processor to perform logical steps of the methods of the invention. The computer software products include a computer readable medium having computer-executable instructions for analyzing, manipulating, transforming and displaying the genetic data in a meaningful and simplified manner to a user.

BACKGROUND OF THE INVENTION

Single nucleotide polymorphism (SNP) has been used extensively for genetic analysis. Fast and reliable hybridization-based SNP assays have been developed. (See, Wang et al., *Science,* 280:1077-1082, 1998; Gingeras, et al., *Genome Research,* 8:435-448, 1998; and Halushka, et al., *Nature Genetics,* 22:239-247, 1999; incorporated herein by reference in their entireties). Computer-implemented methods for discovering polymorphism and determining genotypes are disclosed in, for example, U.S. Pat. No. 5,858,659, incorporated herein by reference in its entirety for all purposes. However, there is still need for additional methods for determining genotypes and displaying the large amount of genetic information obtained from such experiments in a user-friendly interactive computer application.

Users often require that a genetic segment be of a certain size to be of interest and accepted as a true positive, e.g. reflective or indicative of a biologically relevant genetic event. This demand has triggered the ability to computationally smooth and/or join and/or otherwise mathematically manipulate genetic data.

The interpretation of gene copy number abnormalities, e.g. gains or losses of the number of copies of a specific gene relative to a normal population reference, may be performed in a qualitative manner using ratios of changes of sequence per chromosome that are aligned with a linear position. These qualitative assessments, to date, do not incorporate a measurement for a typical population variation, e.g. Copy Number Variation (CNV). The software applications disclosed herein are capable of identifying the start and stop linear positions for each segmental aberration, quantifying the number of interrogating markers, e.g. number of genetic markers being analyzed, comprised of the CN aberration, combining the start and stop linear positions into a CN aberration, or segment size estimate, which includes the density of markers within the region, and estimating the percentage of reported population CNVs within the segment based on external database information. These features allow for the assessment of disease-related copy number aberrations versus copy number abnormalities which are normally found in the population but do not cause a phenotype or biological effect.

This disclosed software addresses these issues by allowing the user to define "CytoRegions" of special interest within genetic data displayed by the software program of the invention, which allows the user to modify the results by an additional data filtering process, which can be of greater or lesser stringency than the data filtering applied to the rest of the genome outside of the user-defined CytoRegions.

BRIEF SUMMARY OF THE INVENTION

There is a demand among users of probe arrays and others for methods and systems for organizing, accessing, analyzing, simplifying and succinctly displaying the vast amount of genetic information collected using nucleic acid probe arrays or using other types of probe arrays. For example, described herein are software programs enabling the display of only specific regions of the chromosome tested to simplify and render more visually accessible large quantities of genetic data. One such software program or system is described in the publication "Affymetrix Chromosome Analysis Suite 1.0 User Manual," available on the internet from the Affymetrix website at the URL Affymetrix.com (Affymetrix, Inc., Santa Clara, Calif.), which is incorporated herein by reference in all of its entirety for all purposes. Systems, methods, and computer program products are described herein to address these and other needs. While certain systems, methods, and computer software products are described using exemplary embodiments for analyzing data from experiments that employ GENECHIP™ probe arrays from Affymetrix, Inc., or spotted arrays, these systems, methods, and products may be applied with respect to other probe arrays and parallel biological assays.

In some embodiments, a method for analyzing molecules by enabling a user-provided application to access data structures is described. The probe molecules of such probe arrays may include nucleic acids including synthesized nucleic acids, locked nucleic acid (LNA) or other nucleic acid analogs, and peptides, polysaccharides or analogues thereof. The probe array may also include a spotted array.

In some implementations, the method may include enabling target molecules found in an experimental sample to interact with probe molecules. The target molecules may include biological materials such as cells, proteins, genes, polypeptides, oligonucleotides, polynucleotides, nucleic acids, expressed sequence tags (EST's), or other DNA sequences, ligands or receptors.

Additionally, in some implementations the code libraries include an object type library, and executable code callable from the user-provided application. The applications programming interface may hide the format of the data files, and may be downloadable from a remote source. The code libraries may enable export of data elements to a standardized format that includes a MicroArray and Gene Expression (MAGE)—Markup Language (ML), or a similar format.

In some embodiments, the method may further include storing the pixel data, the intermediate results data, or both, in one or more data files. The software applications described herein may have many different features, including, but not limited to, segmentation and differential filtering capabilities, as described further below.

In some implementations the data files utilized by the described software programs may include a .DAT-type file, a .CEL-type file, a .CHP-type file (including .CYCHP and .CNCHP), a .CDF-type file, a .BED and/or .AED file, among others. The data file type is not critical, but rather the type of data contained in the file should be data pertaining to intensity measurements corresponding to hybridization of target to probe nucleic acids. For instance, the data elements may include probe set data, quality control data, probe array name, x and y coordinate data, probe array type data, sample data, hybridization data, scan data, corner feature data, intensity data by probe position, intensity data by line, algorithm parameter data, probe intensity data by index, probe intensity data by position, probe intensity data by index and position, standard deviation data, pixel data, outlier data, masked feature data, background quality control data, header data, probe set data including data by index or all probe sets, statistical results, empirical results, probe pair data including intensity by x and y coordinates, perfect match probes, mismatch probes, background intensity, or quality control data.

In some implementations, the number of biological experiments is more than one, and the code libraries further enable batch transfer of the pixel data, the intermediate results data, or both, from the more than one biological experiments. The biological experiments may include experiments using a synthesized array or a spotted array, or alternatively using a synthesized array and a spotted array. The data structure may conform to a published database schema that could include the integrated database AADM schema, and that could be included in a laboratory information management system.

In some implementations, the described software application may include a data-mining tool, an image-processing tool, or a data-processing tool. Additionally, the described software application could include a data-processing tool that may further include the functions of determining degrees of hybridization, determining absolute expression of genes or EST's, determining differential expression over two or more experiments of genes or EST's, making genotype comparisons, detecting polymorphisms, or detecting mutations.

Additionally, in some implementations, the code libraries may enable the use of high or low level programming languages including Java, C++, Visual C++, Visual Basic, ASP (Active Server Pages), ASP.NET, .NET C#, VB, VB.NET and various frameworks such as ATL, MFC, .NET, Winforms, .NET WFP, and others. Any such programming language may be used, so long as the language is capable of performing various mathematical calculations as required, explained in further detail below. The code libraries may also enable transfer of pixel data, intermediate results data, or both, from at least one data element from one or more data files directly or indirectly to a user-provided application.

Embodiments of the user-provided application may include computer software which displays the genetic data obtained from the experiments in various formats, styles, segments and filtering-depending modes. The display may be in color and may be interactive, allowing the user to define various functionalities and various segments of gene or genomic regions. These described software applications may display a map of the entire genome. The genome may be human, mouse, insect, plant, bacterial or any other type of genome from the various kingdoms of life for which a probe array is available for experimentation.

The genetic map displayed to the user by the software program may be in color and particularly may make use of various colors to signify different functionalities, genetic features, alleles or any other such characteristic. Furthermore, the software application may enable a user to interface directly with the genomic map obtained from the data, which may display, for instance, the identities of the various SNP's sequences by the genetic experiment(s). The software program may also interface directly or by clicking on a mouse connected to a computer which is connected to internet genetic databases, such as the OMIM™ database (Johns Hopkins University), such that a user can access genetic functional data through the software program.

The software programs disclosed herein, in particular embodiments, may allow the user to differentially filter genetic data, such as copy number data, by entering specific parameters designed to define the CytoRegions of interest to the user. Other parameters may be entered which define genetic regions or segments lying outside of the CytoRegions. The filtering is performed by the user by entering specific desired values or parameters that are utilized by the software and various included algorithms to identify genetic events. Alternatively, the user may make these value selections by moving visual sliding controls or bars within the browser software. The segments appear and disappear as the filtering is adjusted by the user. Any number of visual representation means may be utilized to allow the user to manually adjust the segment filter values and to view the results of the filtering in real time, as the values are adjusted, in all three panes of the Display Area window.

The described software programs, in particular embodiments, may employ various mathematical algorithms and software code to implement the desired transformation of the data for visual inspection to the user. The software programs may accept the user-defined parameters and based on these parameters, manipulate or otherwise modify the genetic information, such that the display presented to the user for visual inspection simply and succinctly provides the user with the specific information desired via the differential filtering of the genetic data lying within and outside of the defined CytoRegions.

The above implementations are not necessarily inclusive or exclusive of each other and may be combined in any manner that is non-conflicting and otherwise possible, whether they be presented in association with a same, or a different, aspect or implementation. The description of one implementation is not intended to be limiting with respect to other implementations. Also, any one or more function, step, operation, or technique described elsewhere in this specification may, in alternative implementations, be combined with any one or more function, step, operation, or technique described in the summary. Thus, the above implementations are illustrative rather than limiting.

BRIEF DESCRIPTION OF THE DRAWINGS

The above and further features will be more clearly appreciated from the following detailed description when taken in conjunction with the accompanying drawings. In functional block diagrams, rectangles generally indicate functional elements and parallelograms generally indicate data. In method flow charts, rectangles generally indicate method steps and diamond shapes generally indicate decision elements. All of these conventions, however, are intended to be typical or illustrative, rather than limiting.

DETAILED DESCRIPTION

I. General Description

Figure 1:
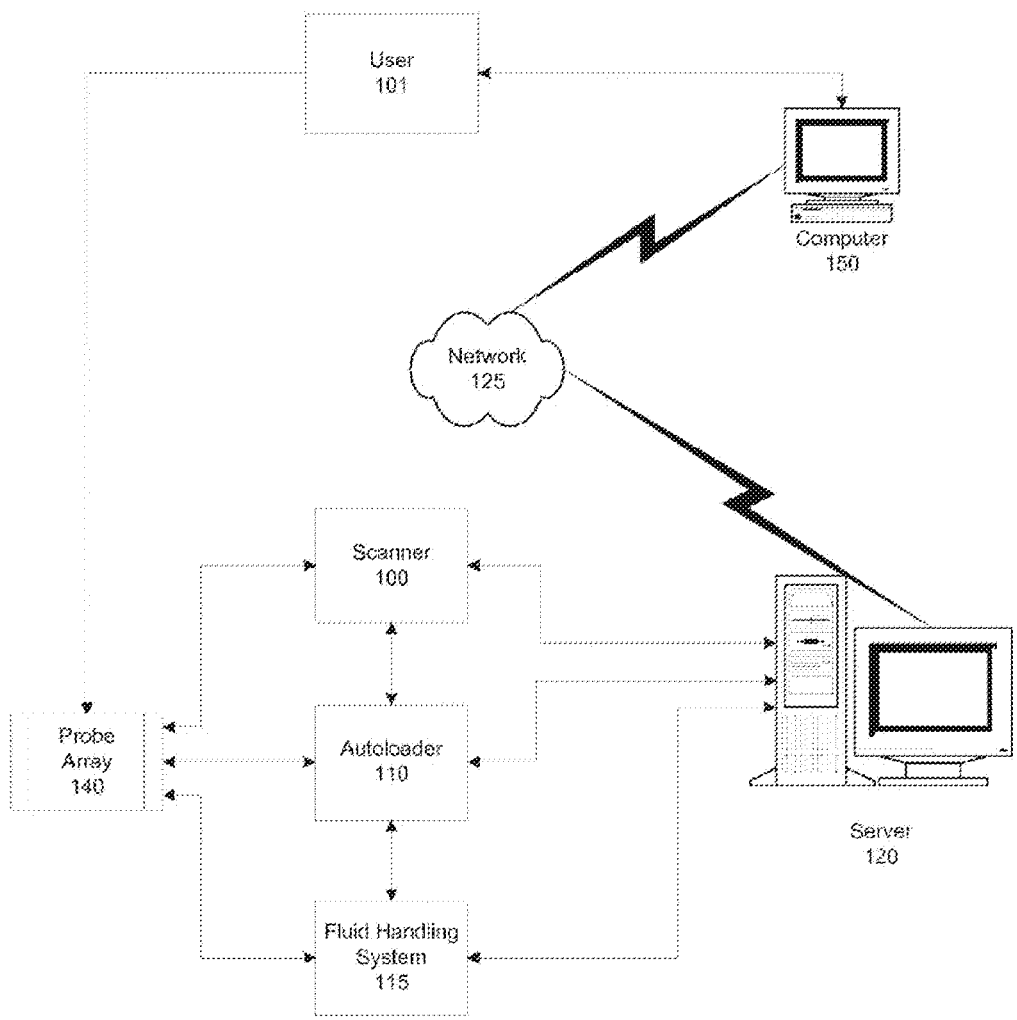
FIG. 1 is a functional block diagram of one embodiment of a computer and a server enabled to communicate over a network, as well as a probe array and probe array instruments.

Reference will now be made in detail to exemplary embodiments of the invention. While the invention will be described in conjunction with the exemplary embodiments, it will be understood that they are not intended to limit the invention to these embodiments. On the contrary, the invention is intended to encompass alternatives, modifications and equivalents, which may be included within the spirit and scope of the invention.

The invention relates to diverse fields impacted by the nature of molecular interaction, including chemistry, biology, medicine and diagnostics. Methods disclosed herein are advantageous in fields, such as those in which genetic information is required quickly, as in clinical diagnostic laboratories or in large-scale undertakings such as the Human Genome Project.

The invention described herein has many embodiments and relies on many patents, applications and other references for details known to those of the art. Therefore, when a patent, application, or other reference is cited or repeated below, it should be understood that the entire disclosure of the document cited is incorporated by reference in its entirety for all purposes as well as for the proposition that is recited. All documents, e.g., publications and patent applications, cited in this disclosure, including the foregoing, are incorporated herein by reference in their entireties for all purposes to the same extent as if each of the individual documents were specifically and individually indicated to be so incorporated herein by reference in its entirety.

As used in this application, the singular form "a," "an," and "the" include plural references unless the context clearly dictates otherwise. For example, the term "an agent" includes a plurality of agents, including mixtures thereof.

An individual is not limited to a human being but may also be other organisms including, but not limited to, mammals, plants, bacteria, or cells derived from any of the above.

Throughout this disclosure, various aspects of this invention can be presented in a range format. It should be understood that when a description is provided in range format, this is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6, for example, as well as individual numbers within that range, for example, 1, 2, 3, 4, 5, and 6. This applies regardless of the breadth of the range.

The practice of the invention described herein may employ, unless otherwise indicated, conventional techniques and descriptions of organic chemistry, polymer technology, molecular biology (including recombinant techniques), cell biology, biochemistry, and immunology, which are within the skill of one of skill in the art. Such conventional techniques include polymer array synthesis, hybridization, ligation, and detection of hybridization using a detectable label. Specific illustrations of suitable techniques are provided by reference to the examples hereinbelow. However, other equivalent conventional procedures may also be employed. Such conventional techniques and descriptions may be found in standard laboratory manuals, such as *Genome Analysis: A Laboratory Manual Series (Vols. I-IV)*, *Using Antibodies: A Laboratory Manual, Cells: A Laboratory Manual, PCR Primer: A Laboratory Manual,* and *Molecular Cloning: A Laboratory Manual* (all from Cold Spring Harbor Laboratory Press), Stryer, L. (1995), *Biochemistry*, 4th Ed., Freeman, N.Y., Gait, *Oligonucleotide Synthesis: A Practical Approach*, (1984), IRL Press, London, Nelson and Cox (2000), Lehninger, *Principles of Biochemistry*, $3^{rd}$ Ed., W.H. Freeman Pub., New York, N.Y., and Berg et al. (2002), *Biochemistry*, $5^{th}$ Ed., W.H. Freeman Pub., New York, N.Y., all of which are herein incorporated in their entirety by reference for all purposes.

The invention may employ solid substrates, including arrays in some embodiments. Methods and techniques applicable to polymer (including protein) array synthesis have been described in U.S. Ser. No. 09/536,841 (abandoned), WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, and in PCT Applications Nos. PCT/US99/00730 (International Publication No. WO 99/36760) and PCT/US01/04285 (International Publication No. WO 01/58593), which are all incorporated herein by reference in their entirety for all purposes.

Patents that describe synthesis techniques in specific embodiments include U.S. Pat. Nos. 5,412,087, 6,147,205, 6,262,216, 6,310,189, 5,889,165, and 5,959,098. Nucleic acid arrays are described in many of the above patents, but the same techniques are applied to polypeptide arrays.

Nucleic acid arrays that are useful in the described invention include, but are not limited to, those that are commercially available from Affymetrix (Santa Clara, Calif.) under the brand name GENECHIP®. Example arrays are shown on the Affymetrix website at the URL affymetrix.com.

Many uses for polymers attached to solid substrates are contemplated herein. These uses include, but are not limited to, gene expression monitoring, profiling, library screening, genotyping and diagnostics. Methods of gene expression monitoring and profiling are described in U.S. Pat. Nos. 5,800,992, 6,013,449, 6,020,135, 6,033,860, 6,040,138, 6,177,248 and 6,309,822. Genotyping methods, and uses thereof, are disclosed in U.S. patent application Ser. No. 10/442,021 (abandoned) and U.S. Pat. Nos. 5,856,092, 6,300,063, 5,858,659, 6,284,460, 6,361,947, 6,368,799, 6,333,179, and 6,872,529. Other uses are described in U.S. Pat. Nos. 5,871,928, 5,902,723, 6,045,996, 5,541,061, and 6,197,506.

Also contemplated are sample preparation methods in certain embodiments. Prior to, or concurrent with, genotyping, the genomic sample may be amplified by a variety of mechanisms, some of which may employ PCR. (See, for example, *PCR Technology: Principles and Applications for DNA Amplification*, Ed. H. A. Erlich, Freeman Press, NY, N.Y., 1992; *PCR Protocols: A Guide to Methods and Applications*, Eds. Innis, et al., Academic Press, San Diego, Calif., 1990; Mattila et al., *Nucleic Acids Res.*, 19:4967, 1991; Eckert et al., *PCR Methods and Applications*, 1:17, 1991; *PCR*, Eds. McPherson et al., IRL Press, Oxford, 1991; and U.S. Pat. Nos. 4,683,202, 4,683,195, 4,800,159 4,965,188, and 5,333,675, each of which is incorporated herein by reference in their entireties for all purposes. The sample may also be amplified on the array. (See, for example, U.S. Pat. No. 6,300,070 and U.S. patent application Ser. No. 09/513,300 (abandoned), all of which are incorporated herein by reference).

Other suitable amplification methods include the ligase chain reaction (LCR) (see, for example, Wu and Wallace, *Genomics*, 4:560 (1989), Landegren et al., *Science*, 241: 1077 (1988) and Barringer et al., *Gene*, 89:117 (1990)), transcription amplification (Kwoh et al., *Proc. Natl. Acad. Sci. USA*, 86:1173 (1989) and WO 88/10315), self-sustained sequence replication (Guatelli et al., *Proc. Nat. Acad. Sci. USA*, 87:1874 (1990) and WO 90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909 and 5,861,245) and nucleic acid based sequence amplification (NABSA). (See also, U.S. Pat. Nos. 5,409, 818, 5,554,517, and 6,063,603, each of which is incorporated herein by reference). Other amplification methods that may be used are described in, for instance, U.S. Pat. Nos. 6,582,938, 5,242,794, 5,494,810, and 4,988,617, each of which is incorporated herein by reference.

Additional methods of sample preparation and techniques for reducing the complexity of a nucleic sample are described in Dong et al., *Genome Research*, 11:1418 (2001), U.S. Pat. Nos. 6,361,947, 6,391,592, 6,632,611, 6,872,529 and 6,958,225, and in U.S. patent application Ser. No. 09/916,135 (abandoned).

Methods for conducting polynucleotide hybridization assays have been well developed in the art. Hybridization assay procedures and conditions will vary depending on the application and are selected in accordance with known general binding methods, including those referred to in Maniatis et al., *Molecular Cloning: A Laboratory Manual*, $2^{nd}$ Ed., Cold Spring Harbor, N.Y., (1989); Berger and Kimmel, *Methods in Enzymology, Guide to Molecular Cloning Techniques*, Vol. 152, Academic Press, Inc., San Diego, Calif. (1987); Young and Davism, *Proc. Nat'l. Acad. Sci.*, 80:1194 (1983). Methods and apparatus for performing repeated and controlled hybridization reactions have been described in, for example, U.S. Pat. Nos. 5,871,928, 5,874, 219, 6,045,996, 6,386,749, and 6,391,623 each of which are incorporated herein by reference.

The invention also provides signal detection of hybridization between ligands in certain embodiments. (See, U.S. Pat. Nos. 5,143,854, 5,578,832, 5,631,734, 5,834,758, 5,936,324, 5,981,956, 6,025,601, 6,141,096, 6,185,030, 6,201,639, 6,218,803, and 6,225,625, U.S. patent application Ser. No. 10/389,194 (U.S. Patent Application Publication No. 2004/0012676, allowed) and PCT Application PCT/US99/06097 (published as WO 99/47964), each of which is hereby incorporated by reference in its entirety for all purposes).

The practice of the inventions herein may also employ conventional biology methods, software and systems. Computer software products of the invention typically include, for instance, computer readable medium having computer-executable instructions for performing the logic steps of the method of the invention. Suitable computer readable medium include, but are not limited to, a floppy disk, CD-ROM/DVD/DVD-ROM, hard-disk drive, flash memory, ROM/RAM, magnetic tapes, and others that may be developed. The computer executable instructions may be written in a suitable computer language or combination of several computer languages. Basic computational biology methods which may be employed in the invention are described in, for example, Setubal and Meidanis et al., *Introduction to Computational Biology Methods*, PWS Publishing Company, Boston, (1997); Salzberg, Searles, Kasif, (Ed.), *Computational Methods in Molecular Biology*, Elsevier, Amsterdam, (1998); Rashidi and Buehler, *Bioinformatics Basics: Application in Biological Science and Medicine*, CRC Press, London, (2000); and Ouelette and Bzevanis *Bioinformatics: A Practical Guide for Analysis of Gene and Proteins*, Wiley & Sons, Inc., $2^{nd}$ ed., (2001). (See also, U.S. Pat. No. 6,420,108).

The invention may also make use of various computer program products and software for a variety of purposes, such as probe design, management of data, analysis, and instrument operation. (See, U.S. Pat. Nos. 5,593,839, 5,795, 716, 5,733,729, 5,974,164, 6,066,454, 6,090,555, 6,185,561, 6,188,783, 6,223,127, 6,229,911 and 6,308,170).

Additionally, the invention encompasses embodiments that may include methods for providing genetic information over networks such as the internet, as disclosed in, for instance, U.S. patent application Ser. No. 10/197,621 (U.S. Patent Application Publication No. 20030097222), Ser. No. 10/063,559 (U.S. Patent Application Publication No. 20020183936, abandoned), Ser. No. 10/065,856 (U.S. Patent Application Publication No. 20030100995, abandoned), Ser. No. 10/065,868 (U.S. Patent Application Publication No. 20030120432, abandoned), Ser. No. 10/328,818 (U.S. Patent Application Publication No. 20040002818, abandoned), Ser. No. 10/328,872 (U.S. Patent Application Publication No. 20040126840, abandoned), Ser. No. 10/423,403 (U.S. Patent Application Publication No. 20040049354, abandoned), and 60/482,389 (expired).

II. Definitions of Selected Terms

The term "array" as used herein refers to an intentionally created collection of molecules which can be prepared either synthetically or biosynthetically. The molecules in the array can be identical or different from each other. The array can assume a variety of formats, e.g., libraries of soluble molecules; libraries of compounds tethered to resin beads, silica chips, or other solid supports.

The term "biomonomer" as used herein refers to a single unit of biopolymer, which can be linked with the same or other biomonomers to form a biopolymer (for example, a single amino acid or nucleotide with two linking groups one or both of which may have removable protecting groups) or a single unit which is not part of a biopolymer. Thus, for example, a nucleotide is a biomonomer within an oligonucleotide biopolymer, and an amino acid is a biomonomer within a protein or peptide biopolymer; avidin, biotin, antibodies, antibody fragments, and others, for example, are also biomonomers.

The term "biopolymer" or "biological polymer" as used herein is intended to mean repeating units of biological or chemical moieties. Representative biopolymers include, but are not limited to, nucleic acids, oligonucleotides, amino acids, proteins, peptides, hormones, oligosaccharides, lipids, glycolipids, lipopolysaccharides, phospholipids, synthetic analogues of the foregoing, including, but not limited to, inverted nucleotides, peptide nucleic acids, Meta-DNA, and combinations of the above.

The term "biopolymer synthesis" as used herein is intended to encompass the synthetic production, both organic and inorganic, of a biopolymer. Related to a biopolymer is a "biomonomer".

The term "complementary" as used herein refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa Nucleic Acids Res. 12:203 (1984), incorporated herein by reference.

The term "complex population or mixed population" as used herein refers to any sample containing both desired and undesired nucleic acids. As a non-limiting example, a complex population of nucleic acids may be total genomic DNA, total genomic RNA or a combination thereof. Moreover, a complex population of nucleic acids may have been enriched for a given population but include other undesirable populations. For example, a complex population of nucleic acids may be a sample which has been enriched for desired messenger RNA (mRNA) sequences but still includes some undesired ribosomal RNA sequences (rRNA).

The term "effective amount" as used herein refers to an amount sufficient to induce a desired result.

The term "genome" as used herein is all the genetic material in the chromosomes of an organism. DNA derived from the genetic material in the chromosomes of a particular organism is genomic DNA. A genomic library is a collection of clones made from a set of randomly generated overlapping DNA fragments representing the entire genome of an organism.

The term "hybridization conditions" as used herein will typically include salt concentrations of less than about 1M, more usually less than about 500 mM and preferably less than about 200 mM. Hybridization temperatures can be as low as 5° C., but are typically greater than 22° C., more typically greater than about 30° C., and preferably in excess of about 37° C. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone.

The term "hybridization" as used herein refers to the process in which two single-stranded polynucleotides bind non-covalently to firm a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." Hybridizations are usually performed under stringent conditions, for example, at a salt concentration of no more than 1 M and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations. For stringent conditions, see, for example, Sambrook, Fritsche and Maniatis, "Molecular Cloning A laboratory Manual" $2^{nd}$ Ed. Cold Spring Harbor Press (1989), which is hereby incorporated by reference in its entirety for all purposes above.

Hybridizations, e.g., allele-specific probe hybridizations, are generally performed under stringent conditions. For example, conditions where the salt concentration is no more than about 1 Molar (M) and a temperature of at least 25° C., e.g., 750 mM NaCl, 50 mM Sodium Phosphate, 5 mM EDTA, pH 7.4 (5×SSPE) and a temperature of from about 25 to about 30° C.

The term "hybridization probes" as used herein are oligonucleotides capable of binding in a base-specific manner to a complete a strand of nucleic acid. Such probes include peptide nucleic acids, as described in Nielsen et al., *Science*, 254, 1497-1500 (1991), and other nucleic acid analogs and nucleic acid mimetics.

The term "hybridizing specifically to" as used herein refers to the binding, duplexing, or hybridizing of a molecule only to a particular nucleotide sequence or sequences under stringent conditions when that sequence is present in a complex mixture (e.g., total cellular) DNA or RNA.

The term "initiation biomonomer" or "initiator biomonomer" as used herein is meant to indicate the first biomonomer which is covalently attached via reactive nucleophiles to the surface of the polymer, or the first biomonomer which is attached to a linker or spacer arm attached to the polymer, the linker or spacer arm being attached to the polymer via reactive nucleophiles.

The term "isolated nucleic acid" as used herein mean an object species invention that is the predominant species present (e.g., on a molar basis it is more abundant than any other individual species in the composition). Preferably, an isolated nucleic acid comprises at least about 50, 80 or 90% (on a molar basis) of all inacromotecular species present. Most preferably, the object species is purified to essential homogeneity (contaminant species cannot be detected in the composition by conventional detection methods).

The term "ligand" as used herein refers to a molecule that is recognized by a particular receptor. The agent bound by or reacting with a receptor is called a "ligand," a term which is definitionally meaningful only in terms of its counterpart receptor. The term "ligand" does not imply any particular molecular size or other structural or compositional feature other than that the substance in question is capable of binding or otherwise interacting with the receptor. Also, a ligand may serve either as the natural ligand to which the receptor binds, or as a functional analogue that may act as an agonist or antagonist. Examples of ligands that can be investigated by this invention include, but are not restricted to, agonists and antagonists for cell membrane receptors, toxins and venoms, viral epitopes, hormones (e.g., opiates, steroids, and other similar compounds), hormone receptors, peptides, enzymes, enzyme substrates, substrate analogs, transition state analogs, cofactors, drugs, proteins, and antibodies.

The term "linkage disequilibrium" or "allelic association" as used herein refers to the preferential association of a particular allele or genetic marker with a specific allele, or genetic marker at a nearby chromosomal location more frequently than expected by chance for any particular allele frequency in the population. For example, if locus X has alleles a and b, which occur equally frequently, and linked locus Y has alleles c and d, which occur equally frequently, one would expect the combination ac to occur with a frequency of 0.25. If ac occurs more frequently, then alleles a and c are in linkage disequilibrium. Linkage disequilibrium may result from natural selection of certain combination of alleles or because an allele has been introduced into a population too recently to have reached equilibrium with linked alleles.

The term "mixed population" as used herein refers to a complex population.

The term "monomer" as used herein refers to any member of the set of molecules that can be joined together to form an oligomer or polymer. The set of monomers useful in this invention includes, but is not restricted to, for the example of (poly)peptide synthesis, the set of L-amino acids, D-amino acids, or synthetic amino acids. As used herein, "monomer" refers to any member of a basis set for synthesis of an oligomer. For example, dimers of L-amino acids form a basis set of 400 "monomers" for synthesis of polypeptides. Different basis sets of monomers may be used at successive steps in the synthesis of a polymer. The term "monomer" also refers to a chemical subunit that can be combined with a different chemical subunit to form a compound larger than either subunit alone.

The term "mRNA" or "mRNA transcripts" as used herein, include, but not limited to pre-mRNA transcript(s), transcript processing intermediates, mature mRNA(s) ready for translation and transcripts of the gene or genes, or nucleic acids derived from the mRNA transcript(s). Transcript processing may include splicing, editing and degradation. As used herein, a nucleic acid derived from an mRNA transcript refers to a nucleic acid for whose synthesis the mRNA transcript or a subsequence thereof has ultimately served as a template. Thus, a cDNA reverse transcribed from an mRNA, an RNA transcribed from that cDNA, a DNA amplified from the cDNA, an RNA transcribed from the amplified DNA, for example, are all derived from the mRNA transcript and detection of such derived products is indicative of the presence and/or abundance of the original transcript in a sample. Thus, mRNA derived samples include, but are not limited to, mRNA transcripts of the gene or genes, cDNA reverse transcribed from the mRNA, cRNA transcribed from the cDNA, DNA amplified from the genes, RNA transcribed from amplified DNA, and the like.

The term "nucleic acid library or array" as used herein refers to an intentionally created collection of nucleic acids which can be prepared either synthetically or biosynthetically and screened for biological activity in a variety of different formats (e.g., libraries of soluble molecules; and libraries of oligos tethered to resin beads, silica chips, or other solid supports). Additionally, the term "array" is meant to include those libraries of nucleic acids which can be prepared by spotting nucleic acids of essentially any length (e.g., from 1 to about 1000 nucleotide monomers in length) onto a substrate. The term "nucleic acid" as used herein refers to a polymeric form of nucleotides of any length, either ribonucleotides, deoxyribonucleotides, locked nucleic acids (LNAs) or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleoside sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

The term "nucleic acids" as used herein may include any polymer or oligomer of pyrimidine and purine bases, preferably cytosine, thymine, and uracil, and adenine and guanine, respectively. (See, Albert L. Lehninger, "Principles of Biochemistry," at 793-800, Worth Pub. 1982). Indeed, the invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally-occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

The term "oligonucleotide" or "polynucleotide" as used interchangeably herein refers to a nucleic acid ranging from at least 2, preferable at least 8, and more preferably at least 20 nucleotides in length or a compound that specifically hybridizes to a polynucleotide. Polynucleotides of the invention include sequences of deoxyribonucleic acid (DNA) or ribonucleic acid (RNA) which may be isolated from natural sources, recombinantly produced or artificially synthesized and mimetics thereof. A further example of a polynucleotide of the invention may be locked nucleic acids (LNAs) or peptide nucleic acid (PNA). The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application.

The term "probe" as used herein refers to a surface-immobilized molecule that can be recognized by a particular target. See U.S. Pat. No. 6,582,908 for an example of arrays having all possible combinations of probes with 10, 12, and more bases. Examples of probes that can be investigated by this invention include, but are not restricted to, agonists and antagonists for cell membrane receptors, toxins and venoms, viral epitopes, hormones (e.g., opioid peptides, steroids), hormone receptors, peptides, enzymes, enzyme substrates, cofactors, drugs, lectins, sugars, oligonucleotides, nucleic acids, oligosaccharides, proteins, and monoclonal antibodies.

The term "primer" as used herein refers to a single-stranded oligonucleotide capable of acting as a point of initiation for template-directed DNA synthesis under suitable conditions e.g., buffer and temperature, in the presence of four different nucleoside triphosphates and an agent for polymerization, such as, for example, DNA or RNA polymerase or reverse transcriptase. The length of the primer, in any given case, depends on, for example, the intended use of the primer, and generally ranges from 15 to 30 nucleotides. Short primer molecules generally require cooler temperatures to form sufficiently stable hybrid complexes with the template. A primer need not reflect the exact sequence of the template but must be sufficiently complementary to hybridize with such template. The primer site is the area of the template to which a primer hybridizes. The primer pair is a set of primers including a 5' upstream primer that hybridizes with the 5' end of the sequence to be amplified and a 3' downstream primer that hybridizes with the complement of the 3' end of the sequence to be amplified.

The term "polymorphism" as used herein refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphism may comprise one or more base changes, an insertion, a repeat, or a deletion. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms. Single nucleotide polymorphisms (SNPs) are included in polymorphisms.

The term "receptor" as used herein refers to a molecule that has an affinity for a given ligand. Receptors may be naturally-occurring or manmade molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. As the term receptors is used herein, no difference in meaning is intended. A "Ligand Receptor Pair" is formed when two macromolecules have combined through molecular recognition to form a complex. Other examples of receptors which can be investigated by this invention include but are not restricted to those molecules shown in U.S. Pat. No. 5,143,854, which is hereby incorporated by reference in its entirety.

The term "solid support", "support", and "substrate" as used herein are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. (See, U.S. Pat. No. 5,744,305 for exemplary substrates).

The term "target" as used herein refers to a molecule that has an affinity for a given probe. Targets may be naturally-occurring or man-made molecules. Also, they can be employed in their unaltered state or as aggregates with other species. Targets may be attached, covalently or noncovalently, to a binding member, either directly or via a specific binding substance. Examples of targets which can be employed by his invention include, but are not restricted to, antibodies, cell membrane receptors, monoclonal antibodies and antisera reactive with specific antigenic determinants (such as on viruses, cells or other materials), drugs, oligonucleotides, nucleic acids, peptides, cofactors, lectins, sugars, polysaccharides, cells, cellular membranes, and organelles. Targets are sometimes referred to in the art as anti-probes. As the term targets is used herein, no difference in meaning is intended. A "Probe Target Pair" is formed when two macromolecules have combined through molecular recognition to form a complex.

A "translocation" or "chromosomal translocation" is a chromosome abnormality caused by rearrangement of parts between nonhomologous chromosomes. It is detected on cytogenetics or a karyotype of affected cells. There are two main types, reciprocal (also known as non-Robertsonian) and Robertsonian. Also, translocations can be balanced (in an even exchange of material with no genetic information extra or missing, and ideally full functionality) or unbalanced (where the exchange of chromosome material is unequal resulting in extra or missing genes).

A karyotype is the observed characteristics (number, type, shape etc) of the chromosomes of an individual or species.

In normal diploid organisms, autosomal chromosomes are present in two identical copies, although polyploid cells have multiple copies of chromosomes and haploid cells have single copies. The chromosomes are arranged and displayed (often on a photo) in a standard format known as an idiogram: in pairs, ordered by size and position of centromere for chromosomes of the same size. Karyotypes are used to study chromosomal aberrations, and may be used to determine other macroscopically visible aspects of an individual's genotype, such as sex. In order to be able to see the chromosomes and determine their size and internal pattern, they are chemically labeled with a dye ("stained"). The pattern of individual chromosomes is called chromosome banding.

Normal human karyotypes contain 22 pairs of autosomal chromosomes and one pair of sex chromosomes. Normal karyotypes for women contain two X chromosomes and are denoted 46,XX; men have both an X and a Y chromosome denoted 46,XY.

A single-nucleotide polymorphism (SNP) is a DNA sequence variation occurring when a single nucleotide—A, T, C, or G—in the genome (or other shared sequence) differs between members of a species (or between paired chromosomes in an individual). For example, two sequenced DNA fragments from different individuals, AAGCCTA to AAGCTTA, contain a difference in a single nucleotide. In this case we say that there are two alleles: C and T. Almost all common SNPs have only two alleles.

Loss of Heterozygosity (LOH) represents the loss of normal function of one allele of a gene in which the other allele was already inactivated. In oncology, loss of heterozygosity occurs when the remaining functional allele in a somatic cell of the offspring becomes inactivated by mutation. This results in no normal tumor suppressor being produced and this could result in tumorigenesis. Zygosity is the similarity of genes for a trait (inherited characteristic) in an organism. If both genes are the same, the organism is homozygous for the trait. If both genes are different, the organism is heterozygous for that trait. If one gene is missing, it is hemizygous, and if both genes are missing, it is nullizygous. The DNA sequence of any gene can vary among individuals in the population. The various forms of a gene are called alleles, and diploid organisms generally have two alleles for each gene, one on each of the two homologous chromosomes on which the gene is present. In diploid organisms, the alleles are inherited from the individual's parents, one from the male parent and one from the female. Zygosity in general is a description of whether those two alleles have identical or different DNA sequences. For cytogeneticists, detection of LOH is important because such genetic abnormalities may be associated with genetic disorders.

In particular, a major focus in cytogenetics research is on Uniparental Disomy (UPD) events where a child inherits two copies of chromosomal material from one parent and nothing from the other. These UPD events are known to be linked with recessive disorders and also cause developmental disorders due to gene imprinting. These events occur without associated copy number changes. For instance approximately 30% of Prader-Willi cases are associated with paternal UPD of chromosome 15q, 2-3% of Angelman Syndrome are associated with maternal UPD of 15q, 10-30% of Beckwith-Wiedemann Syndrome are associated with maternal UPD of 11p15, and 5% of Silver-Russell Syndrome are associated with maternal UPD of chromosome 7.

LOH is also known to be associated with consanguinity and inbreeding. The boundary between the two of these genetic events is not always clear. Generally, consanguinity refers to close relation matings producing off-spring, e.g. first cousin pairings. This will tend to result in large blocks of LOH, perhaps on only a few chromosomes. Inbreeding refers to small isolated (perhaps physically or culturally) populations where the degree of genetic variability is low within the population. This may lead to many small blocks of LOH across many chromosomes.

Long Contiguous Stretches of Homozygosity (LCSH) in a genomic region (stretch) indicates a region in which the Copy Number is neutral (two copies) but which displays a Loss of normal heterozygosity, and thus is homozygous for the measured SNP allele information.

A Segment, as used hereinbelow, is a visual or tabular representation of a biological or other type of event in genetic material. Segments are derived from discrete data points in linear genomic space by examining the values of contiguous discrete data points, especially those data points which diverge from a reference "normal" data value. Segment boundaries can be comprised of the coordinate data from, at, or immediately adjacent to, two or more such discrete data points. Segments have a start marker and an end marker and a discrete size typically measured in nucleotide base pairs. Segments may also be called genetic segments or data segments. Segments may be smoothed and/or joined by protocols defined in further detail below. Segments may also be filtered by user-based inputs into the software program of the invention. Elimination of segments containing fewer than a minimum threshold of genetic markers (markers) is achieved by assigning the markers in small segments to larger neighboring segments. No markers are removed from the output, so this is not an output filter and the user need not be concerned with missing markers. Setting the minimum segment size to a value of one would disable this feature of the presently disclosed software program.

Filtering or differential filtering is the action of a user of setting of threshold values to enable differential display, or inclusion or exclusion, of a segment or segments of a particular type in a data set, based on whether the segment's or segments' values meet or do not meet the threshold value for a parameter. The parameters defined by the user are entered by the user into the software program disclosed herein. The parameters upon which filtering can be performed are possessed by segments, and can be used for the purpose of defining which segments will appear or be included in a particular set of data with a particular set of Filter settings. Filtering may be based on many different types of genetic, parameters, such as, but not limited to, number of markers, length of genetic sequence, overlap map/overlap, and confidence value/score. Such filters may be applied to a single segment type or all segment types, however the segments may be defined, using different parameters for each type. Filtering parameters, once entered or changed by the user, are immediately applied to the data so that immediate results of the filtering are visualized by the user.

An overlap map is a file containing a genetic sequence map of the genome of interest in the form of data, such as a region information file, typically in the AED or BED file format. The overlap map file contains position information for various genetic markers, and may be obtained from reference annotation files. An overlap map file can be used to hide segments in areas of the genome that the user is not interested in viewing in the software disclosed herein. These regions might be, for example, areas of chromosomes of Common Nucleotide Polymorphism. Thus, the overlap map can be used by the user, once entered into the software and applied as a filter across the data, to screen out genetic regions of no interest to the user or having no unusual genetic variability or characteristics. Thus, detected segments may be filtered out of the display of experimental data visualized by the software for the user, making the segments left to be visualized more prominently displayed and easier to visually inspect by the user. The software disclosed herein may allow the user o specify the percentage of the segment, e.g. between 1% and 100%, that must be overlapped by the overlap map to be filtered out by the application of the overlap map to the experimental data. This overlap map filter is separate and distinguishable from the CytoRegions features defined or definable by the user. Different overlap map filtering parameters may be applied to CytoRegions as compared to parameters applied to areas outside of CytoRegions, offering the user much flexibility altering the displayed data for easier visual inspection.

A copy number variation (CNV) is a segment of DNA in which copy number differences have been found by comparison of two or more genomes. The segment may range from one kilobase to several megabases in size. Humans (being normally diploid) ordinarily have two copies of each autosomal region of genetic material, one per chromosome. This may vary for particular genetic regions due to deletion or duplication events. CNVs may either be inherited or caused by de novo mutation. CNVs can be caused by genomic rearrangements such as deletions, duplications, inversions, and translocations.

Low copy repeats (LCRs), which are region-specific repeat sequences, are susceptible to such genomic rearrangements resulting in CNVs. Factors such as size, orientation, percentage similarity and the distance between the gene copies renders them susceptible.

Copy Number Polymorphism (CNP) analysis is a specialized method for determining the copy number state in specific genomic CNP regions. CNP regions are observed to be more variable in copy number state than the genome as a whole. Because the copy number state in CNP regions is more likely to deviate from the normal copy number state of two, previous copy number analysis methods were less accurate when applied to CNP regions. Therefore, a new analysis algorithm called Canary was developed by researchers at the Broad Institute for copy number analysis within CNP regions.

A Browser Extensible Data (BED) file format provides a flexible way to define data lines that are displayed in an annotation track. BED files have three required fields and nine additional optional fields. The number of fields per line must be consistent throughout any single set of data in an annotation track.

The first three required BED fields are:
 1. chrom—The name of the chromosome (e.g. chr3, chrY, chr2_random) or scaffold (e.g. scaffold10671).
 2. chromStart—The starting position of the feature in the chromosome or scaffold. The first base in a chromosome is numbered 0.
 3. chromEnd—The ending position of the feature in the chromosome or scaffold. The chromEnd base is not included in the display of the feature. For example, the first 100 bases of a chromosome are defined as chromStart=0, chromEnd=100, and span the bases numbered 0-99.

The 9 additional optional BED fields are:
 4. name—Defines the name of the BED line. This label is displayed to the left of the BED line in the Genome Browser window when the track is open to full display mode or directly to the left of the item in pack mode.
 5. score—A score between 0 and 1000. If the track line useScore attribute is set to 1 for this annotation data set, the score value will determine the level of gray in which this feature is displayed (higher numbers=darker gray).
 6. strand—Defines the strand – either '+' or '−'.
 7. thickStart—The starting position at which the feature is drawn thickly (for example, the start codon in gene displays).
 8. thickEnd—The ending position at which the feature is drawn thickly (for example, the stop codon in gene displays).
 9. reserved—This should always be set to zero.
 10. blockCount—The number of blocks (exons) the BED line.
 11. blockSizes—A comma-separated list of the block sizes. The number of items in this list should correspond to blockCount.
 12. blockStarts—A comma-separated list of block starts. All of the blockStart positions should be calculated relative to chromStart. The number of items in this list should correspond to blockCount.

An example of an annotation track that properly uses a complete BED definition is as follows:
  track name=pairedReads description="Clone Paired Reads" useScore=1
  chr22 1000 5000 cloneA 960+1000 5000 0 2 567,488, 0,3512
  chr22 2000 6000 cloneB 900−2000 6000 0 2 433,399, 0,3601

An Affymetrix Extensible Data (AED) file contains a list of annotations, descriptions of features on a biological sequence such as a chromosome. This description is comprised of several properties. The properties are defined by, for instance, the annotation start and stop positions, or are defined by the user or other third parties. An AED file may also provide metadata which describe the particular group of annotations in the file as a whole, such as the author of the file or the genome assembly for which the annotations were produced. Properties and metadata have certain types which define the semantics and constrain the range of values they may have. Properties generally begin with a lowercase letter, while types generally begin with an uppercase letter. The AED file format uses a tab-delimited text format with the *.aed file extension. It uses Unicode character sets. An AED file has the following components: a) header row: names the properties that can be used in the annotations, b) metadata (optional): provides information about the AED file itself and the group of annotations it contains, and c) annotations: for each feature annotated, an annotation row provides values for the properties listed in the header rows. The header row of an AED file is a tab-delimited list of the properties that can be used to describe a region of the genome. Each AED file header represents a property. Normal records in the file represent annotations, and the record fields represent annotation properties. Special metadata records represent metadata properties for the file as a whole, rather than for a particular annotation. For additional information on AED files and their uses within the context of the presently claimed inventions, please see "Affymetrix Chromosome Analysis Suite 1.0 User Manual" available on the internet from the Affymetrix website at the URL Affymetrix.com, which is incorporated herein by reference in all of its entirety for all purposes.

An Annotation track provides information about the genetic code to which it is attached. For instance, an annotation track may provide the user with visual information indicating whether a selected segment of the genome displays LOH, LCSH or any other such genetic characteristic or abnormality.

A Hidden Markov Model (HMM) is a statistical model where the system being modeled is assumed to be a Markov process with unknown parameters, and the challenge is to determine the hidden parameters from the observable parameters. HMM statistical models are used by the disclosed invention software application to determine whether, for instance, there is a change in Copy Number State. The extracted model parameters can then be used to perform further analysis, for example, for pattern recognition applications. A HMM can be considered as the simplest dynamic Bayesian network. In a regular Markov model, the state is directly visible to the observer, and therefore the state transition probabilities are the only parameters. In a hidden Markov model, the state is not directly visible, but variables influenced by the state are visible. Each state has a probability distribution over the possible output value. Therefore the sequence of values generated by an HMM gives some information about the sequence of states, e.g. Copy Number States. Hidden Markov models are especially known for their application in temporal pattern recognition such as speech, handwriting, gesture recognition and bioinformatics. (See, for instance, Lior Pachter and Bernd Sturmfels, "Algebraic Statistics for Computational Biology," Cambridge University Press, 2005, ISBN 0-521-85700-7; Eddy, *Nature Biotechnology*, 22:1315-1316 (2005) and Pavel Pevzner, "Computational Molecular Biology: An Algorithmic Approach," MIT Press, 2000, especially pp. 145-149; see also, Rabiner, L., "A Tutorial on Hidden Markov Models and Selected Applications in Speech Recognition," *Proceedings of the IEEE*, Volume 77, pp 257-86, 1989). A HMM is typically defined by a set of hidden states, a matrix of state transition probabilities and a matrix of emission probabilities. Each hidden state has different statistical properties. (See, U.S. patent application Ser. No. 12/143,754, corresponding to U.S. Patent Application Publication No. 2009/0098547, incorporated herein by reference for purposes). Application of the HMM model to genetic data may yield, for instance, a set of reported probabilities at each defined genetic marker of whether the marker is either normal or abnormal in copy number. Such probabilities may be summarized by the disclosed software application for entire segments.

Basically, the HMM processes data one chromosome at a time; a single chromosome is input, a copy number is assigned to each marker, then the markers are partitioned into contiguous segments. A brief summary of the process may be represented as follows. First, summaries are computed at each pre-defined genetic marker based on the likelihood function of the model. The likelihood-based summary provides the probability of the marker belonging to each of the copy number categories, but ignores the same probabilities at neighboring markers. Second, the HMM combines probabilities of markers by taking into account probabilities of neighboring markers as well as probabilities of copy number state transitions from one marker to the next. The result is a chain of copy number calls, one call at each marker, extending the length of the chromosome. The transition probabilities may be specified ahead of time and act independent of the data. Third, of the many possible chains of copy number calls that could be simultaneously assigned to an entire chromosome of markers, the chain with the highest probability is reported to the user, and later displayed to the user by the software application. Finally, the chain of copy number calls is partitioned into segments such that each copy number segment has an identical copy number call at each marker. End points of segments therefore indicate a change in copy number call.

A CytoRegion is a linear genomic sequence region of interest to a cytogeneticist or other biological scientist (user). Cytoregion(s) can be defined by designating one or more data file(s) (BED, AED, and by reference annotation data base files) containing coordinate information as the cytoregion file. CytoRegions may start and stop anywhere defined by the user, and may even start and stop in the middle of identified segments (see above for definition of segments).

An Expressed Sequence Tag (EST) is a short sub-sequence of a transcribed cDNA sequence. They may be used to identify gene transcripts, and are instrumental in gene discovery and gene sequence determination. The identification of ESTs has proceeded rapidly, with approximately 52 million ESTs available in public databases as of 2008 (e.g. GenBank, and others).

Mosaicism, is the presence of differing genetic sequences or composition within a specified region of the genome. Copy Number Mosaicism indicates the experimental sample genetic marker in question has a copy number which is not a whole integer, but rather is a fractional number, e.g. the copy number is determined by the software and analysis to not be one or two, but is instead determined empirically from the experimental sample to be, for example, a value of 1.6.

AP Plot Frequency is a variable that provides the algorithm with the number of SNPs to skip up for each allele peak. It should be a positive integer starting from 1. The maximum allowable input for this parameter is between 200,000 and 1000. At a value of 100, allele peaks may be calculated at every 100th SNP (using the window size defined by AP Minimum Markers, below). At 1, allele peaks are calculated at every SNP.

AP Minimum Markers are the number of markers in each window used to find allele peaks. The larger this parameter is, the less variation there is of allele peaks. However, it should not be set to be too large, otherwise, the markers that represent the local biological events, such as LOH, will be averaged out by their neighboring non-LOH markers. The maximum allowable input for this parameter is between 5000 and 500.

AP Bandwidth Factor represents variation of bandwidth choice and is used for the density estimation for the allele plot. (See, Scott, D. W. (1992) "Multivariate Density Estimation: Theory, Practice, and Visualization," Wiley). Because this bandwidth is likely to be too large for the density estimator to pick up small local biological events, it is recommended to adjust the bandwidth by this factor. In general, larger AP Bandwidth Factor values results in fewer peaks and vice versa. This input must be a decimal number between 0.01 and 1.

Diagonal Weight is a copy number parameter referring to the values on the diagonal of the HMM transition matrix. This weight can take on a value in the range (0,1) and it acts as a penalty for changing copy number state from one marker to the next in either direction. A diagonal weight of 0 would force a change in copy number to always happen. Likewise a diagonal weight of 1 would never allow a change to occur. These extremes are not accepted by the Affymetrix Power Tools (APT) application, which executes the HMM methods described elsewhere. The default value is close to 1 and discourages frequent changes in copy number but short runs of markers with values indicating a copy number change will overcome this weight as will large outliers. Given the noise level in copy number data it makes no sense to use a diagonal weight below about 0.9. This will overload output with too many segments. Setting the diagonal weight too close to 1 to not produce short segments can cause spurious segments of non-normal copy number. It may be simplest in some cases to eliminate short segments by post processing the segmentation.

MAPD is the Median Absolute Pairwise Difference statistic. MAPD is defined as the Median of the Absolute values of all Pairwise Differences between $\log_2$ ratios for a given probe array. Each pair is defined as adjacent in terms of genomic distance, with SNP markers and CN markers being treated equally. Hence, any two markers that are adjacent in the genomic coordinates are a pair. Except at the beginning and the end of a chromosome, every marker belongs to two pairs as it is adjacent to a marker preceding it and a marker following it on the genome. Formally, if xi: is the log 2 ratio for marker i:

$$\text{MAPD}=\text{median}(|x_{i+1}-x_i|, i \text{ ordered by genomic position})$$

MAPD is a per-chip estimate of variability, like standard deviation (SD) or interquartile range (IQR). If the log 2 ratios are distributed normally with a constant SD, then MAPD/0.96 is equal to SD and MAPD*1.41 is equal to IQR. However, unlike SD or IQR, using MAPD is robust against high biological variability in log 2 ratios induced by conditions such as cancer.

MAPD Weight is also a copy number parameter, which is used to add the Median Absolute Pairwise Difference statistic to the dispersion parameter Standard Deviation found in Copy Number Parameters:HMM Parameters:Priors. If the MAPD weight is increased from the default, it makes sense to decrease the Standard Deviation.

Min Segment Size is a copy number parameter used to control reporting of small segments by APT. The markers in any segments shorter than the minimum size specified will have their copy number assignments imputed to conform with neighboring segments that are at least as large as the minimum size.

Mean is a copy number parameter which lists the expected values of the log base 2 ratios with respect to the reference sample corresponding to each copy number state. It is best to have the means as accurate as possible, however, it is difficult to estimate the copy number means of any sample from within the sample.

Standard Deviation is a copy number parameter that lists the corresponding expected standard deviations in the $\log_2$ ratio data corresponding to each copy number state. Note that MAPD is computed for each sample and added to these standard deviations after MAPD is multiplied by the MAPD weight.

GC Correction is an algorithm that removes variation using a non-parametric method that matches probe set intensities given chromosomal GC content to the reference. Some samples are subject to variation that is linked to regional variation in chromosomal GC content.

LOH Minimum Information (T_min) is a variable which controls the size of the windows used by the algorithm. An attempt is made to determine whether each, in each window, LOH is detected. The larger this value the larger the size of the windows used, e.g. it can be used to reduce the number of small regions detected. An algorithm nay be used which dynamically selects the value that is used for optimal performance. Alternatively, the user may enter a value for this variable which is only used if the algorithm selects a smaller value than the user. The units of this quantity is based on assigning each marker a weight based on its expected level of performance. Thus, this quantity is the total information content required in a region to be able to make a determination of LOH.

LOH Critical Value is the cut-off value for the test statistic used to determine whether LOH is present in a given region of the genome. A value higher than 0 means that it is likely LOH is present. Increasing this value reduces the number of false positives but will decrease resolution. The scale on this quantity is logarithmic. So a value of 1 means LOH is 2.71 times more likely than non-LOH, and a value of 10 means LOH is approximately 22,000 times more likely than non-LOH.

Integer Copy Number State (CNState, or CNS) values are determined in series for each chromosome within the genome of the experimental genetic sample to find "segments" where chromosomal material has incurred a gain or loss material. Such gains and losses of chromosomal material may then be displayed as a segment defined by the user. Other processes may be involved in defining segments, such as smoothing multiple aberrations into a single "segment" or joining segments over normal data to make a single segment out of multiple initial segments.

Smoothing as used herein refers to a process of manipulating the data found in user-defined Segments (defined below). For instance, smoothing of Copy Number segments can take place when more than one adjacent segment has an aberrant copy number call. For example, if there is a stretch of twenty markers with copy number three, followed by a stretch of five markers with copy number four, followed by a stretch of ten markers with copy number three. These three segments that are together are an uninterrupted copy number gain. The three segments can be smoothed into one, in which case. Smoothing only takes place over stretches that are entirely a gain or entirely a loss. As another example, consider a set of data having a contiguous set of segments with gain values (for instance, of CNState values of three and four), with no markers of copy number two or lower. Without smoothing, these segments will be treated and represented by the software application as a series of individual gain segments. The same rules apply to a set of segments with loss values of 0 or 1. If within the data there is present a contiguous set of markers with gain values of three and four, with no intervening markers of copy number two or lower, then these data will be consolidated into a single gain segment with smoothing applied. It is important to note that smoothing is only a visual aid to the user and does not affect the actual values (data file, like a .chp file) used as the input in the HMM process. The actual values remain unchanged in the data file for later use.

Joining is also an optional manipulation of genetic data that can be performed on the Copy Number Segment data. Joining can occur when two or more otherwise contiguous aberrant copy number segments of the same copy number are interrupted by a normal copy number segment. For example, if there is a stretch of 15 markers with copy number 3 is interrupted by 5 markers called as normal, followed by 25 markers with copy number 3. The 3 segments can be joined into one copy number gain by ignoring the short normal stretch. The short ignored stretch is treated as missing. Joining options within the software application allow the user to join segments with the same aberrant CNState that are separated by no more than a user-specified number of normal-state markers, or by no more than a user-specified distance of normal-state data.

Smoothing and Joining are non-destructive mathematical processes that affect the display of Copy Number segments. Smoothing and Joining are performed on the CNState data as it is loaded into the software application, based on settings that the user sets before loading. These processes do not affect the marker data in the .cnchp/.cychp files (explained in further detail below).

Generally, confidence parameter values are generated during scanning of the probe array and included in the .cychp data file. This parameter indicates the length of the segment and the number of markers per unit length. The confidence parameter therefore is a measure of the likelihood that the segment represents a real change in the sequence of the genome as compared with a standard or normal or control sample. This confidence score may need to be recalculated during segment detection based on various mathematical algorithm applications, such as smoothing or joining.

Below are provided various terms and variables explaining generally how the software application of the invention may work and may be implemented. Though these embodiments may be very specific, it is understood by one of skill in the art that many modifications may be made of these specifications to achieve the same general outcome. All of these generally known and acknowledged alternative embodiments are incorporated herein within the scope of this disclosed invention.

III. Specific Embodiments of the Invention—System

This invention relates to software that accepts, analyzes and visually presents data obtained from nucleic acid probe microarrays, such as AFFYMETRIX GENECHIP® probe arrays, and spotted probe arrays. The data is signal intensities obtained from scans of the probe arrays hybridized with test samples. These biological microarrays have been used to generate unprecedented amounts of information about biological systems. For example, the Affymetrix Genome-Wide Human SNP Array 6.0, available from Affymetrix, Inc. of Santa Clara, Calif., contains 1.8 million oligonucleotides, with over 900,000 probes dedicated to detection of SNPs, and over 900,000 probes dedicated to detection of non-SNP markers and copy number variations. Analysis of expression and genotype data from such microarrays may lead to the development of new drugs and new diagnostic tools.

By way of example, the invention is described as it applies to a four-peg instrumentation, but it should be recognized that the invention has a broader range of applicability. (See, for instance, U.S. Pat. Nos. 5,445,934; 5,744,305; 5,945,334; 6,140,044; 6,261,776; 6,291,183; 6,346,413; 6,399,365; 6,420,169; 6,551,817; 6,610,482; 6,733,977; 6,955,915; D430,024; 5,445,934; 5,744305; 6,261,776; 6,291,183; 6,346,413; 6,399,365; 6,610,482; 6,733,977 concerning various arrays; U.S. Pat. Nos. 6,114,122; 6,287,850; 6,391,623; and 6,422,249 concerning various fluidics stations; U.S. Pat. Nos. 5,578,832; 5,631,734; 5,834,758; 5,936,324; 5,981,956; 6,025,601; 6,141,096; 6,171,793; 6,185,030; 6,201,639; 6,207,960; 6,218,803; 6,225,625; 6,252,236; 6,335,824; 6,403,320; 6,407,858; 6,472,671; 6,490,533; 6,650,411; 6,643,015; 6,813,567; 6,141,096; 6,262,838; 6,294,327; 6,403,320; 6,407,858; 6,597,000; and 7,406,391 concerning various scanners; U.S. Pat. Nos. 6,511,277; 6,604,902; 6,705,754; and 7,108,472 concerning various auto-loading devices useful with the instrumentation and software of the present invention; all incorporated herein by reference for all purposes in their entirety).

A biological microarray often includes nucleic acid probes that are used to extract sequence information from nucleic acid samples. The nucleic acid samples are exposed to the nucleic acid probes under certain conditions that allow hybridization. The sample nucleic acids may be labeled with a detectable chemical moiety, such as a fluorescent dye, or signal obtained from an enzyme-linked assay. Afterwards, the biological microarray is processed and scanned. The location of the signal indicates which probes hybridized to the nucleic acid samples. Based on such determination, the sequence information is obtained by comparing patterns of hybridization and non-hybridization. As an example, the sequence information can be used for sequencing nucleic acids, or diagnostic screening for genetic diseases or for detecting the presence of a particular pathogen or a strain of pathogen.

Various techniques and technologies may be used for synthesizing dense arrays of biological materials on or in a substrate or support. For example, the Affymetrix GENECHIP™ arrays are synthesized in accordance with techniques sometimes referred to as VLSPS™ (Very Large Scale Immobilized Polymer Synthesis) technologies. Some aspects of VLSPS™ and other microarray manufacturing technologies are described in U.S. Pat. Nos. 5,424,186; 5,143,854; 5,445,934; 5,744,305; 5,831,070; 5,837,832; 6,022,963; 6,083,697; 6,291,183; 6,309,831; and 6,310,189, all of which are hereby incorporated by reference in their entireties for all purposes. The probes of these arrays in some implementations consist of nucleic acids that are synthesized by methods including the steps of activating regions of a substrate and then contacting the substrate with a selected monomer solution. As used herein, nucleic acids may include any polymer or oligomer of nucleosides or nucleotides (polynucleotides or oligonucleotides) that include pyrimidine and/or purine bases, preferably cytosine, thymine, and uracil, and adenine and guanine, respectively. Nucleic acids may include any deoxyribonucleotide, ribonucleotide, and/or peptide nucleic acid component, and/or any chemical variants thereof such as LNAs, methylated, hydroxymethylated or glucosylated forms of these bases, and the like. The polymers or oligomers may be heterogeneous or homogeneous in composition, and may be isolated from naturally-occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states. Probes of other biological materials, such as peptides or polysaccharides as non-limiting examples, may also be formed. For more details regarding possible implementations, see U.S. Pat. No. 6,156,501, which is hereby incorporated by reference herein in its entirety for all purposes.

A system and method for efficiently synthesizing probe arrays using masks is described in U.S. Pat. No. 6,949,638, which is hereby incorporated by reference herein in its entirety for all purposes. A system and method for a rapid and flexible microarray manufacturing and online ordering system is described in U.S. Provisional Patent Application Ser. No. 60/265,103 (now expired), filed Jan. 29, 2001, which also is hereby incorporated herein by reference in its entirety for all purposes. Systems and methods for optical photolithography without masks are described in U.S. Pat. No. 6,271,957 and in U.S. patent application Ser. No. 09/683,374 filed Dec. 19, 2001 (now abandoned), both of which are hereby incorporated by reference herein in their entireties for all purposes.

The probes of synthesized probe arrays typically are used in conjunction with biological target molecules of interest, such as cells, proteins, genes or EST's, other DNA sequences, or other biological elements. More specifically, the biological molecule of interest may be a ligand, receptor, peptide, nucleic acid (oligonucleotide or polynucleotide of RNA or DNA), or any other of the biological molecules listed in U.S. Pat. No. 5,445,934 (incorporated by reference above) at column 5, line 66 to column 7, line 51. For example, if transcripts of genes are the interest of an experiment, the target molecules would be the transcripts. Other examples include protein fragments and small molecules. Target nucleic acid refers to a nucleic acid (often derived from a biological sample) of interest. Frequently, a target molecule is detected using one or more probes. As used herein, a probe is a molecule for detecting a target molecule. A probe may be any of the molecules in the same classes as the target referred to above. As non-limiting examples, a probe may refer to a nucleic acid, such as an oligonucleotide, capable of binding to a target nucleic acid of complementary sequence through one or more types of chemical bonds, usually through complementary base pairing, usually through hydrogen bond formation. As noted above, a probe may include natural, e.g. A, G, U, C, or T, or modified bases (7-deazaguanosine, inosine, LNA, PNA, for example). In addition, the bases in probes may be joined by a linkage other than a phosphodiester bond, so long as the bond does not interfere with hybridization. Thus, probes may be peptide nucleic acids in which the constituent bases are joined by peptide bonds rather than phosphodiester linkages. Other examples of probes include antibodies used to detect peptides or other molecules, any ligands for detecting its binding partners. When referring to targets or probes as nucleic acids, it should be understood that these are illustrative embodiments that are not to limit the invention in any way.

The samples or target molecules of interest (hereafter, simply targets) are processed so that, typically, they are spatially associated with certain probes in the probe array. For example, one or more tagged targets are distributed over the probe array. In accordance with some implementations, some targets hybridize with probes and remain at the probe locations, while non-hybridized targets are washed away. These hybridized targets, with their tags or labels, are thus spatially associated with the probes. The hybridized probe and target may sometimes be referred to as a probe-target pair. Detection of these pairs can serve a variety of purposes, such as to determine whether a target nucleic acid has a nucleotide sequence identical to or different from a specific reference sequence. (See, for example, U.S. Pat. No. 5,837,832, referred to and incorporated above). Other uses include gene expression monitoring and evaluation (see, e.g., U.S. Pat. Nos. 5,800,992, 6,040,138, and International Patent App. No. PCT/US98/15151, published as WO99/05323), genotyping (U.S. Pat. No. 5,856,092), or other detection of nucleic acids. The '992, '138, and '092 patents, and publication WO99/05323, are incorporated by reference herein in their entireties for all purposes.

Other techniques exist for depositing probes on a substrate or support. For example, "spotted arrays" are commercially fabricated, typically on microscope slides. These arrays consist of liquid spots containing biological material of potentially varying compositions and concentrations. For instance, a spot in the array may include a few strands of short oligonucleotides in a water solution, or it may include a high concentration of long strands of complex proteins. There are devices that deposit densely packed arrays of biological materials on microscope slides in accordance with these techniques. Aspects of these and other spot arrayers are described in U.S. Pat. Nos. 6,040,193 and 6,136,269, in U.S. Pat. No. 6,955,788, and in International Patent Application No. PCT/US99/00730 (International Publication Number WO 99/36760), all of which are hereby incorporated by reference in their entireties for all purposes. Other techniques for generating spotted arrays also exist. For example, U.S. Pat. No. 6,040,193 to Winkler, et al., is directed to processes for dispensing drops to generate spotted arrays. The '193 patent, and U.S. Pat. No. 5,885,837 to Winkler, also describe the use of micro-channels or micro-grooves on a substrate, or on a block placed on a substrate, to synthesize arrays of biological materials. These patents further describe separating reactive regions of a substrate from each other by inert regions and spotting on the reactive regions. The '193 and '837 patents are hereby incorporated by reference in their entireties. Another technique is based on ejecting jets of biological material to form a spotted array. Other implementations of the jetting technique may use devices such as syringes or piezo electric pumps to propel the biological material. Various other techniques exist for synthesizing, depositing, or positioning biological material onto or within a substrate.

To ensure proper interpretation of the term "probe" as used herein, it is noted that contradictory conventions exist in the relevant literature. The word "probe" is used in some contexts to refer not to the biological material that is synthesized on a substrate or deposited on a slide, as described above, but to what has been referred to herein as the "target." To avoid confusion, the term "probe" is used herein to refer to probes such as those synthesized according to the VLSPS™ technology; the biological materials deposited so as to create spotted arrays; and materials synthesized, deposited, or positioned on a substrate to form arrays according to other current or future technologies. Thus, microarrays formed in accordance with any of these technologies may be referred to generally and collectively hereafter for convenience as "probe arrays." Moreover, the term "probe" is not limited to probes immobilized in array format. Rather, the functions and methods described herein may also be employed with respect to other parallel assay devices. For example, these functions and methods may be applied with respect to probe-set identifiers that identify probes immobilized on or in beads, optical fibers, or other substrates or media.

Probes typically are able to detect the expression of corresponding genes or EST's by detecting the presence or abundance of mRNA transcripts present in the target. This detection may, in turn, be accomplished by detecting labeled cRNA that is derived from cDNA derived from the mRNA in the target. In general, group of probes, sometimes referred to as a probe set, contains sub-sequences in unique regions of the transcripts and does not correspond to a full gene sequence. Further details regarding the design and use of probes are provided in U.S. Pat. No. 6,188,783, in International Patent Application Ser. No. PCT/US01/02316, filed Jan. 24, 2001, and in U.S. patent application Ser. No. 09/721,042 (abandoned), Ser. No. 09/718,295 (abandoned), and Ser. No. 09/764,324 (abandoned), and U.S. Pat. No. 7,117,095, all of which patents and patent applications are hereby incorporated herein by reference in their entireties for all purposes.

Labeled targets in hybridized probe arrays may be detected using various commercial devices, sometimes referred to as scanners. Scanners image the targets by detecting fluorescent or other emissions from the labels, or by detecting transmitted, reflected, or scattered radiation. A typical scheme employs optical and other elements to provide excitation light and to selectively collect the emissions. Also generally included are various light-detector systems employing photodiodes, charge-coupled devices, photomultiplier tubes, or similar devices to register the collected emissions. For example, a scanning system for use with a fluorescent label is described in U.S. Pat. No. 5,143,854, incorporated by reference above. Other scanners or scanning systems are described in U.S. Pat. Nos. 5,578,832, 5,631,734, 5,834,758, 5,936,324, 5,981,956, 6,025,601, 6,141,096, 6,185,030, 6,490,533, 6,650,411, 6,643,015 and 6,201,639, in International Patent Application PCT/US99/06097 (published as WO99/47964), in U.S. patent application Ser. No. 09/682,837 (abandoned), and in U.S. Provisional Patent Application Ser. No. 60/364,731 (expired), 60/396,457 (expired), and 60/435,178 (expired), each of which patent and patent application is hereby incorporated by reference in its entirety for all purposes.

Embodiments of an image analysis system comprising an image analysis and instrument control application are described herein that provide a flexible and dynamically configurable architecture and a low level of complexity. In particular, embodiments are described that provide file management functionality where each file comprises a unique identifier and logical relationships between the files using those identifiers. Further, the embodiments include a modular architecture for customizing components and functionality to meet individual needs as well as user interfaces provided over a network that provide a less restrictive workflow environment.

Probe Array 140: An illustrative example of probe array 140 is provided in FIGS. 1, 2, and 3. Descriptions of probe arrays are provided above with respect to "Nucleic Acid Probe arrays" and other related disclosure. In various implementations, probe array 140 may be disposed in a cartridge or housing. Examples of probe arrays and associated cartridges or housings may be found in U.S. Pat. Nos. 5,945,334, 6,287,850, 6,399,365, and 6,551,817, each of which is also hereby incorporated by reference in its entirety for all purposes. In addition, some embodiments of probe array 140 may be associated with pegs or posts, where for instance probe array 140 may be affixed via gluing, welding, or other means known in the related art to the peg or post that may be operatively coupled to a tray, strip or other type of similar substrate. Examples with embodiments of probe array 140 associated with pegs or posts may be found in U.S. patent application Ser. No. 10/826,577 (abandoned).

Scanner 100: Labeled targets hybridized to probe arrays may be detected using various devices, sometimes referred to as scanners, as described above with respect to methods and apparatus for signal detection.

An illustrative device is shown in FIG. 1 as scanner 100. For example, scanners image the targets by detecting fluorescent or other emissions from labels associated with target molecules, or by detecting transmitted, reflected, or scattered radiation. A typical scheme employs optical and other elements to provide excitation light and to selectively collect the emissions.

For example, scanner 100 provides a signal representing the intensities (and possibly other characteristics, such as color that may be associated with a detected wavelength) of the detected emissions or reflected wavelengths of light, as well as the locations on the substrate where the emissions or reflected wavelengths were detected. Typically, the signal includes intensity information corresponding to elemental sub-areas of the scanned substrate. The term "elemental" in this context means that the intensities, and/or other characteristics, of the emissions or reflected wavelengths from this area each are represented by a single value. When displayed as an image for viewing or processing, elemental picture elements, or pixels, often represent this information. Thus, in the present example, a pixel may have a single value representing the intensity of the elemental sub-area of the substrate from which the emissions or reflected wavelengths were scanned. The pixel may also have another value representing another characteristic, such as color, positive or negative image, or other type of image representation. The size of a pixel may vary in different embodiments and could include a 2.5 µm, 1.5 µm, 1.0 µm, or sub-micron pixel size. Two examples where the signal may be incorporated into data are data files in the form *.dat or *.tif as generated respectively by Affymetrix Microarray Suite (described in U.S. Pat. No. 7,031,846) based on images scanned from GeneChip® arrays. Examples of scanner systems that may be implemented with embodiments of the invention include U.S. patent application Ser. No. 10/389,194 (allowed), and Ser. No. 11/260,617 (allowed), and U.S. Pat. Nos. 7,148,492 and 7,317,415, each of which are incorporated by reference above.

Autoloader 110: Illustrated in FIG. 1 is autoloader 110 that is an example of one possible embodiment of an automatic loader that provides transport of one or more probe arrays 140 used in conjunction with scanner 100 and fluid handling system 115.

In some embodiments, autoloader 110 may include a number of components such as, for instance, a magazine, tray, carousel, or other means of holding and/or storing a plurality of probe arrays; a transport assembly; and a thermal control chamber. For example, some implementations of autoloader 110 may include features for preserving the biological integrity of the probe arrays for extended periods such as, for instance, a period of up to sixteen hours. Also in the present example, in the event of a power failure or error condition that prevents scanning or other processing steps, autoloader 110 will indicate the failure to user 101 and maintain storage temperature for all probe arrays 140 through the use of what may be referred to as an uninterruptable power supply system. The power failure or other error may be communicated to user 101 by one or more methods that could include audible/visual alarm indicators, a graphical user interface, automated paging system, alert via a graphical user interface provided by instrument control and image analysis applications 372, or other means of automated communication. Still continuing with the present example, the power supply system could also support one or more other systems such as scanner 100 or fluid handling system 115.

Some embodiments of autoloader 110 may include preheating each embodiment of probe array 140 to a preferred temperature prior to or during particular processing or image acquisition operations. For example, autoloader 110 may employ a thermally controlled chamber to pre-heat one or more probe arrays 140 to the same temperature as the internal environment of scanner 100 prior to transport to the scanner. Similarly, autoloader 110 could bring probe array 140 to the appropriate hybridization temperature prior to loading into fluid handling system 115. Also in the present example, autoloader 110 may also employ one or more thermal control operations as post-processing steps such as when autoloader 110 removes each of probe arrays 140 from scanner 100, autoloader 110 may employ one or more environmental or temperature control elements to warm or cool the probe array to a preferred temperature in order to preserve biological integrity.

Many embodiments of autoloader 110 are enabled to provide automated loading/unloading of probe arrays 140 to both fluid handling system 115 and/or scanner 100. Also, some embodiments of autoloader 110 may be equipped with a barcode reader, or other means of identification and information storage such as, for instance, magnetic strips, what are referred to by those of ordinary skill in the related art as radio frequency identification (RFID), or one or more microchips associated with each embodiment of probe array 140. For example, autoloader 110 may read or otherwise identify encoded information from the means of identification and information storage that in the present example may include a barcode associated with probe array 140. Autoloader 110 may use the information and/or identifier directly in one or more operations or alternatively may forward the information and/or identifier to instrument control and image analysis applications 372 of server 120 for processing, where applications 372 may then provide instruction to autoloader 110 based, at least in part, upon the processed information and/or identifier. Also in some implementations, scanner 100 and/or fluid handling system 115 may also be similarly equipped with a barcode reader or other means as described above.

Additional examples of autoloaders and probe array storage instruments are described in U.S. patent application Ser. No. 10/389,194 (allowed) and Ser. No. 10/684,160 (abandoned); and U.S. Pat. Nos. 6,511,277 and 6,604,902 each of which are hereby incorporated by reference in their entireties for all purposes.

Fluid Handling System 115: Embodiments of fluid handling system 115, as illustrated in FIG. 1, may implement one or more procedures or operations for hybridizing one or more experimental samples to probes associated with one or more probe arrays 140, as well as operations that, for instance, may include exposing each of probe arrays 140 to washes, buffers, stains, or other fluids in a sequential or parallel fashion.

Some embodiments of the invention may include probe array 140 enclosed in a housing or cartridge that may be placed in a carousel, tray, or other means of holding for transport or processing as previously described with respect to autoloader 110. For example, a carousel, tray, or carrier may be specifically enabled to register a plurality of probe array 140/housing embodiments in a specific orientation and may enable or improve high throughput processing of each of the plurality of probe arrays 140 by providing positive positional registration so that the robotic instrument may carry out processing steps in an efficient and repeatable fashion. Additional examples of a fluid handling system that interacts with various implementations of probe array 140/housing embodiments is described in U.S. patent application Ser. No. 11/057,320 (abandoned), which is hereby incorporated by reference herein in its entirety for all purposes.

Embodiments of fluid handling system 115 could include a plurality of elements enabled to automatically introduce and remove fluids from a probe array 140 without user intervention such as, for instance, one or more sample holders, fluid transfer devices, and fluid reservoirs. For example, applications 372 may direct fluid handling system 115 to add a specified volume of a particular sample to an associated implementation of probe array 140. In the present example, fluid handling system 115 removes the specified volume of sample from a reservoir positioned in a sample holder via one of the sample transfer pins, pipettes or pipette tips, specialized adaptors, or other means known to those of ordinary skill in the related art. In some embodiments, the sample holder may be thermally controlled in order to maintain the integrity of the samples, reagents, or fluids contained in the reservoirs, for a preferred temperature according to a specific protocol or processing step, or for temperature consistency of the various fluids exposed to probe array 140. The term "reservoir" as used herein could include a vial, tube, bottle, 96 or 384 well plate, or some other container suitable for holding volumes of liquid. Also in the present example, fluid handling system 115 may employ a vacuum/pressure source, valves, and means for fluid transport known to those of ordinary skill in the related art.

In some embodiments, fluid handling system 115 may interface with each of one or more of probe arrays 140 by moving a fluid transfer device such as, for instance, what may be referred to as a pin or needle such as a dual lumen needle, pipette tip, specialized adaptor or other type of fluid transfer device known in the art. For example, as those of ordinary skill in the related art will appreciate, a plurality of fluid transfer devices such as a robotic device comprising a pipettor component coupled to one or more pipette tips may be employed to engage with one or more interfaces or alternatively direct fluid to an exposed surface, in order to process one or more of probe arrays 140, where a plurality of probe arrays 140 may be processed in parallel. In the present example, fluid handling system 115 may simultaneously or in a sequential fashion process a plurality of probe arrays 140 by removing a specified aliquot of sample or other type of fluid from each reservoir disposed in one or more sample holders and deliver each sample or fluid to probe array 140.

Fluid handling system 115 may remove used sample or waste fluids from probe array 140 by, for instance, creating a negative pressure or vacuum through one or more ports associated with a housing. Alternatively, fluids may be similarly expelled using a positive pressure of air, gas, or other type of fluid either alone or in combination with the negative pressure, through one or more ports where the positive pressure may cause the undesired fluid to be expelled through one or more channels or away from an exposed surface. Expelled of removed fluids may be stored in one or more reservoir or alternatively may be expelled from fluid handling system 115 into another waste receptacle or drain. For example, it may be desirable in some implementations for user 101 to recover a sample from probe array 140 and store the recovered sample in an environmentally controlled receptacle in order to preserve the biological integrity.

As those of ordinary skill in the related art will appreciate, the sample content of each reservoir within a sample holder is known so that applications 372 (see FIG. 3) may associate an experimental sample or fluid with a particular embodiment of probe array 140. Fluid handling system 115 may also provide one or more detectors associated with the sample holder to indicate to applications 372 when a reservoir is present or absent. Additionally, fluid handling system 115 may include one or more implementations of a barcode reader, or other means of identification described above with respect to autoloader 110, enabled to identify each reservoir using an associated barcode identifier or other type of machine readable identifier.

Some embodiments of fluid handling system 115 may include one or more detection systems enabled to detect the presence and identity of a fluid associated with probe array 140. Also, some embodiments of fluid handling system 115 may provide an environment that promotes the hybridization of a biological target contained in a sample to the probes of the probe array. Some environmental conditions that affect the hybridization efficiency could include temperature, gas bubbles, agitation, oscillating fluid levels, or other conditions that could promote the hybridization of biological samples to probes. Other environmental conditions that fluid handling system 115 may provide may include a means to provide or improve mixing of fluids. For example a means of shaking probe array 140 to promote inertial movement of fluids and turbulent flow may include what is generally referred to as a plate shaker, rotating carousel, or other shaking instrument. Other sources of fluid mixing could be provided by an ultrasonic source or mechanical source such as for instance a piezo-electric agitation source, or other means of providing mechanical agitation. In the present example, the agitation or shaking means may provide fluidic movement that may improve the efficiency of hybridization of target molecules in a sample to probe array 140. Other examples of elements and methods for mixing fluids in a chamber are provided in U.S. patent application Ser. No.

11/017,095 (abandoned), which is hereby incorporated by reference herein in its entirety for all purposes.

Embodiments of fluid handling system 115 may also perform what those of ordinary skill in the related art may refer o as post hybridization operations such as, for instance, washes with buffers or reagents, water, labels, or antibodies. For example, staining may include introducing a stain comprising molecules with fluorescent tags that selectively bind to the biological molecules or targets that have hybridized to probe array 140. Additional post-hybridization operations may, for example, include the introduction of what is referred to as a non-stringent buffer to probe array 140 to preserve the integrity of the hybridized array.

Some implementations of fluid handling system 115 allow for interruption of operations to insert or remove probe arrays, samples, reagents, buffers, or any other materials. After interruption, fluid handling system 115 may conduct a scan of some or all identifiers associated with probe arrays, samples, carousels, trays, or magazines, user input identifiers, or other identifiers used in an automated process. For example, user 101 may wish to interrupt the process conducted by fluid handling system 115 to remove a tray of samples and insert a new tray. The interruption is communicated to user 101 by a variety of methods, and the user performs the desired tasks. User 101 inputs a command for the resumption of the process that may begin with fluid handling system 115 scanning all available barcode identifiers. Applications 372 determines what has been changed, and makes the appropriate adjustments to procedures aid protocols.

Fluid handling system 115 may also perform operations that do not act directly upon a probe array. Such functions could include the management of fresh versus used reagents and buffers, experimental samples, or other materials utilized in hybridization operations. Additionally, fluid handling system 115 may include features for leak control and isolation from systems that may be sensitive to exposure to liquids. For example, a user may load a variety of experimental samples into fluid handling system 115 that have unique experimental requirements. In the present example the samples may have barcode labels with unique identifiers associated with them. The barcode labels could be scanned with a hand held reader or alternatively fluid handling system 115 could include a dedicated reader. Alternatively, other means of identification could be used as described above. The user may associate the identifier with the sample and store the data into one or more data files. The sample may also be associated with a specific probe array type that is similarly stored.

Additional examples of hybridization and other type of probe array processing instruments are described in U.S. patent application Ser. Nos. 10/684,160 and 10/712,860, both of which are hereby incorporated by reference herein in their entireties for all purposes.

Computer 150: An illustrative example of computer 150 is provided in FIG. 1 and also greater in detail in FIG. 2. Computer 150 may be any type of computer platform such as a workstation, a personal computer, a server, or any other present or future computer. Computer 150 typically includes known components such as a processor 255, an operating system 260, system memory 270, memory storage devices 281, and input-output controllers 275, input-output devices 240, and display devices 245. Display devices 245 may include display devices that provides visual information, this information typically may be logically and/or physically organized as an array of pixels. A Graphical User interface (GUI) controller may also be included that may comprise any of a variety of software programs for providing graphical input and output interfaces, such as for instance GUI's 246, or such as the software programs described in more detail below, which provide differential filtering capabilities. For example, GUI's 246 may provide one or more graphical representations to a user, such as user 101, and also be enabled to process user inputs via GUI's 246 using means of selection or input known to those of ordinary skill in the related art, described in further detail below.

It will be understood by those of ordinary skill in the relevant art that there are many possible configurations of the components of computer 150 and that some components that may typically be included in computer 150 are not shown, such as cache memory, a data backup unit, and many other devices. Processor 255 may be a commercially available processor or it may be one or more different processors that are or will become available. Some embodiments of processor 255 may also include what are referred to as Multi-core processors and/or be enabled to employ parallel processing technology in a single or multi-core configuration. For example, a multi-core architecture typically comprises two or more processor "execution cores." In the present example each execution core may perform as an independent processor that enables parallel execution of multiple threads. In addition, those of ordinary skill in the related will appreciate that processor 255 may be configured in what is generally referred to as 32 or 64 bit architectures, or other architectural configurations now known or that may be developed in the future.

Processor 255 executes operating system 260. Operating system 260 interfaces with firmware and hardware in a well-known manner, and facilitates processor 255 in coordinating and executing the functions of various computer programs that may be written in a variety of programming languages. Operating system 260, typically in cooperation with processor 255, coordinates and executes functions of the other components of computer 150. Operating system 260 also provides scheduling, input-output control, file and data management, memory management, and communication control and related services, all in accordance with known techniques.

System memory 270 may be any of a variety of known or future memory storage devices. Examples include any commonly available random access memory (RAM), magnetic medium such as a resident hard disk or tape, an optical medium such as a read and write compact disc, or other memory storage device. Memory storage devices 281 may be any of a variety of known or future devices, including a compact disk drive, a tape drive, a removable hard disk drive, USB or flash drive, or a diskette drive. Such types of memory storage devices 281 typically read from, and/or write to, a program storage medium (not shown) such as, respectively, a compact disk, magnetic tape, removable hard disk, USB or flash drive, or floppy diskette. Any of these program storage media, or others now in use or that may later be developed, may be considered a computer program product. As will be appreciated, these program storage media typically store a computer software program, such as the programs described in more detail below, and/or data. Computer software programs, also called computer control logic, typically are stored in system memory 270 and/or the program storage device used in conjunction with memory storage device 281.

In some embodiments, a computer program product is described comprising a computer usable medium having control logic (computer software program, including program code) stored therein. The control logic, when executed by processor 255, causes processor 255 to perform functions described herein. In other embodiments, some functions are implemented primarily in hardware using, for example, a hardware state machine. Implementation of the hardware state machine so as to perform the functions described herein will be apparent to those skilled in the relevant arts.

Input-output controllers 275 could include any of a variety of known devices for accepting and processing information from a user, whether a human or a machine, whether local or remote. Such devices include, for example, modem cards, wireless cards, network interface cards, sound cards, or other types of controllers for any of a variety of known input devices. Output controllers of input-output controllers 275 could include controllers for any of a variety of known display devices for presenting information to a user, whether a human or a machine, whether local or remote. In the illustrated embodiment, the functional elements of computer 150 communicate with each other via system bus 290. Some of these communications may be accomplished in alternative embodiments using network or other types of remote communications.

Figure 2:
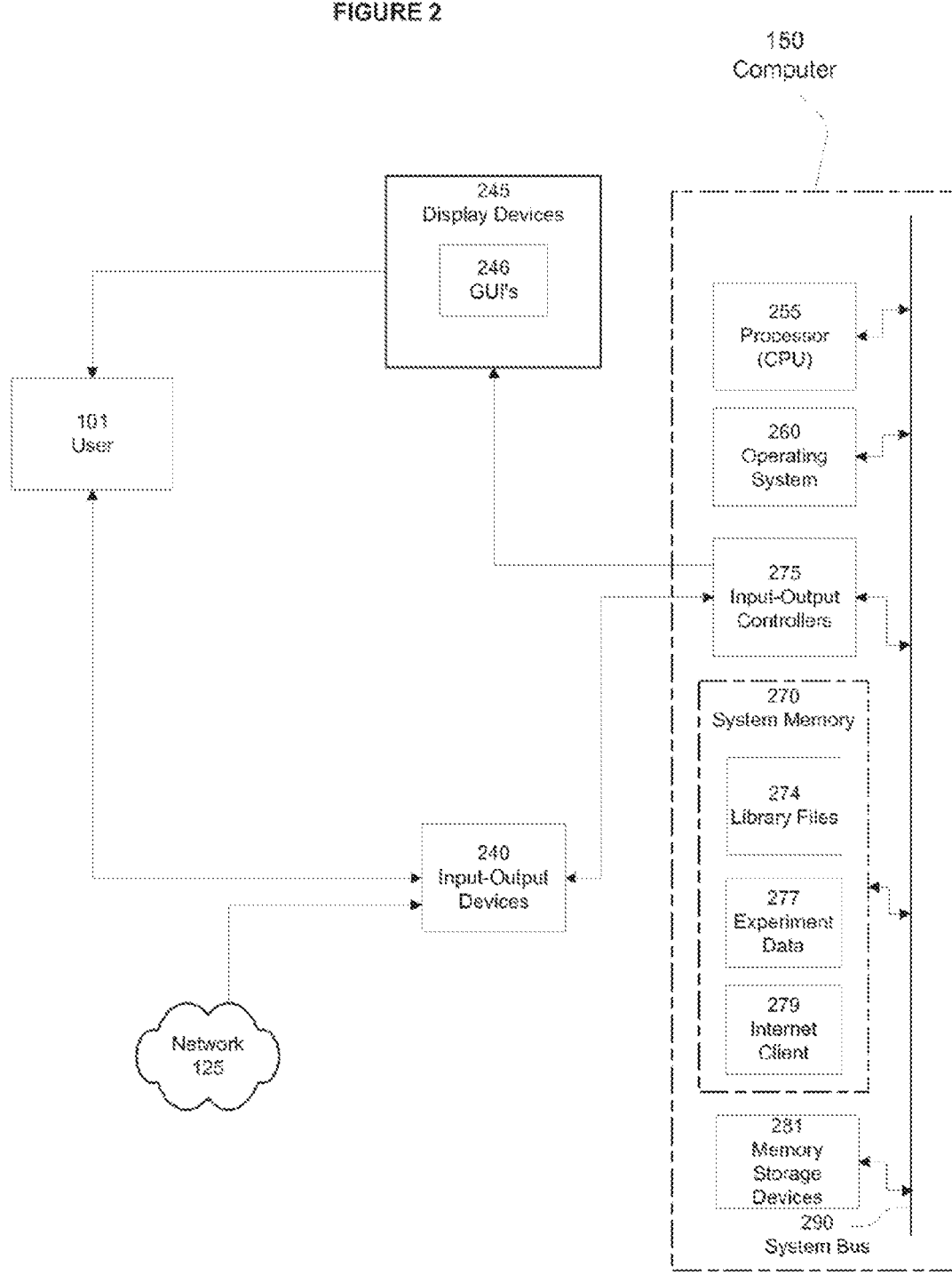
FIG. 2 is a functional block diagram of one embodiment of the computer system of FIG. 1, including a display device that presents a graphical user interface to a user.
Figure 3:
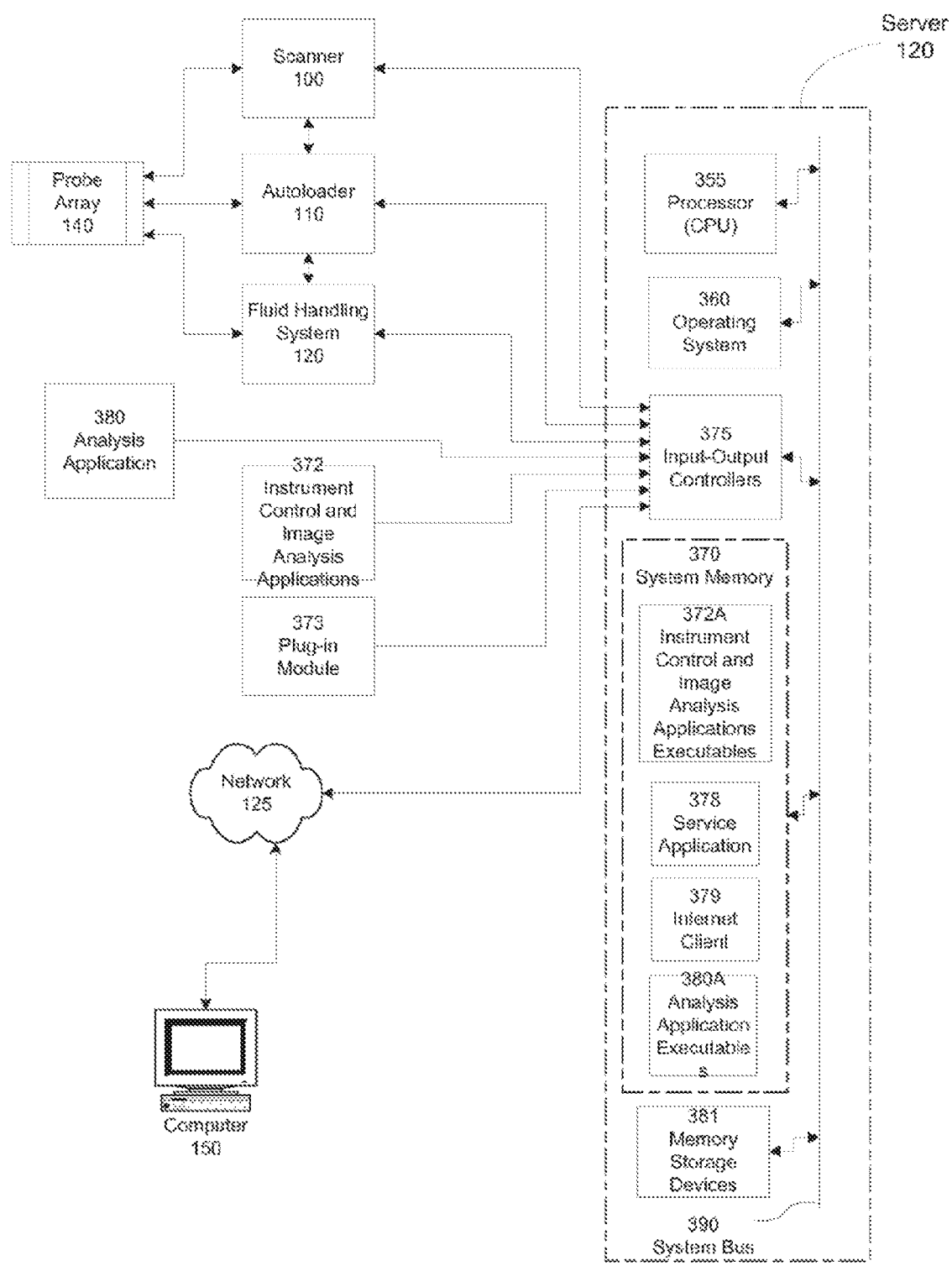
FIG. 3 is a functional block diagram of one embodiment of the server of FIG. 1, where the server comprises an executable instrument control and image analysis application.

As will be evident to those skilled in the relevant art, an instrument control and image processing application, such as for instance an implementation of instrument control and image processing applications 372 illustrated FIG. 3, if implemented in software, may be loaded into and executed from system memory 270 and/or memory storage device 281. All or portions of the instrument control and image processing applications may also reside in a read-only memory or similar device of memory storage device 281, such devices not requiring that the instrument control and image processing applications first be loaded through input-output controllers 275. It will be understood by those skilled in the relevant art that the instrument control and image processing applications, or portions of it, may be loaded by processor 255 in a known manner into system memory 270, or cache memory (not shown), or both, as advantageous for execution. Also illustrated in FIG. 2 are library files 274, experiment data 277, and internet client 279 stored in system memory 270. For example, experiment data 277 could include data related to one or more experiments or assays such as excitation wavelength ranges, emission wavelength ranges, extinction coefficients and/or associated excitation power level values, or other values associated with one or more fluorescent labels. Additionally, interact client 279 may include an application enabled to accesses a remote service on another computer using a network that may for instance comprise what are generally referred to as "Web Browsers." Also, in the same or other embodiments, internet client 279 may include, or could be an element of, specialized software applications enabled to access remote information through a network such as network 125 such as, for instance, the GENECHIP Data Analysis Software (GDAS) package or Chromosome Copy Number Tool (CNAT), both available from Affymetrix, of Santa Clara, Calif., that are each enabled to access information from remote sources, and in particular probe array annotation information from the NETAFFX® web site hosted on one or more servers provided by Affymetrix, Inc. One of skill in the art is aware that there are various gene or genome annotation sites on the internet which may be accessible using software, such as the application described above, and whose information may be displayed by the software for the user's consideration.

Network 125 may include one or more of the many various types of networks well known to those of ordinary skill in the art. For example, network 125 may include a local or wide area network that employs what is commonly referred to as a TCP/IP protocol suite to communicate, that may include a network comprising a worldwide system of interconnected computer networks that is commonly referred to as the internet, or could also include various intranet architectures. Those of ordinary skill in the related arts will also appreciate that some users in networked environments may prefer to employ what are generally referred to as "firewalls" (also sometimes referred to as Packet Filters, or Border Protection Devices) to control information traffic to and from hardware and/or software systems. For example, firewalls may comprise hardware or software elements or some combination thereof and are typically designed to enforce security policies put in place by users, such as for instance network administrators.

Server 120: FIG. 1 shows a typical configuration of a server computer connected to a workstation computer via a network that is illustrated in further detail in FIG. 3. In some implementations any function ascribed to Server 120 may be carried out by one or more other computers, and/or the functions may be performed in parallel by a group of computers.

Typically, server 120 is a network-server class of computer designed for servicing a number of workstations or other computer platforms over a network. However, server 120 may be any of a variety of types of general-purpose computers such as a personal computer, workstation, main frame computer, or other computer platform now or later developed. Server 120 typically includes known components such as processor 355, operating system 360, system memory 370, memory storage devices 381, and input-output controllers 378. It will be understood by those skilled in the relevant art that there are many possible configurations of the components of server 120 that may typically include cache memory, a data backup unit, and many other devices. Similarly, many hardware and associated software or firmware components may be implemented in a network server. For example, components to implement one or more firewalls to protect data and applications, uninterruptible power supplies, LAN switches, web-server routing software, and many other components. Those of ordinary skill in the art will readily appreciate how these and other conventional components may be implemented.

Processor 355 may include multiple processors. Processor 355 executes operating system 360. Some embodiments of processor 355 may also include what are referred to as Multi-core processors and/or be enabled to employ parallel processing technology in a single or multi-core configuration similar to that as described above with respect to processor 255. In addition, those of ordinary skill in the related will appreciate that processor 355 may be configured in what is generally referred to as 32 or 64 bit architectures, or other architectural configurations now known or that may be developed in the future.

Operating system 360 interfaces with firmware and hardware in a well-known manner, and facilitates processor 355 in coordinating and executing the functions of various computer programs that may be written in a variety of programming languages. Operating system 360, typically in cooperation with the processor, coordinates and executes functions of the other components of server 120. Operating system 360 also provides scheduling, input-output control, file and data management, memory management, and communication control and related services, all in accordance with known techniques.

System memory 370 may be any of a variety of known or future memory storage devices. Examples include any commonly available random access memory (RAM), magnetic medium such as a resident hard disk or tape, an optical medium such as a read and write compact disc, or other memory storage device. Memory storage device 381 may be any of a variety of known or future devices, including a compact disk drive, a tape drive, a removable hard disk drive, USB or flash drive, or a diskette drive. Such types of memory storage device typically read from, and/or write to, a program storage medium (not shown) such as, respectively, a compact disk, magnetic tape, removable hard disk, USB or flash drive, or floppy diskette. Any of these program storage media, or others now in use or that may later be developed, may be considered a computer program product. As will be appreciated, these program storage media typically store a computer software program and/or data. Computer software programs, also called computer control logic, typically are stored in the system memory and/or the program storage device used in conjunction with the memory storage device.

In some embodiments, a computer program product is described comprising a computer usable medium having control logic (computer software program, including program code) stored therein. The control logic, when executed by the processor, causes the processor to perform functions described herein. In other embodiments, some functions are implemented primarily in hardware using, for example, a hardware state machine. Implementation of the hardware state machine so as to perform the functions described herein will be apparent to those skilled in the relevant arts.

Input-output controllers 375 could include any of a variety of known devices for accepting and processing information from a user, whether a human or a machine, whether local or remote. Such devices include, for example, modem cards, network interface cards, sound cards, or other types of controllers for any of a variety of known input or output devices. In the illustrated embodiment, the functional elements of server 120 communicate with each other via system bus 390. Some of these communications may be accomplished in alternative embodiments using network or other types of remote communications.

As will be evident to those skilled in the relevant art, a server application if implemented in software, may be loaded into the system memory and/or the memory storage device through one of the input devices, such as instrument control and image processing applications 372 described in greater detail below. All or portions of these loaded elements may also reside in a read-only memory or similar device of the memory storage device, such devices not requiring that the elements first be loaded through the input devices. It will be understood by those skilled in the relevant art that any of the loaded elements, or portions of them, may be loaded by the processor in a known manner into the system memory, or cache memory (not shown), or both, as advantageous for execution.

Instrument control and image processing applications 372: Instrument control and image processing applications 372 may comprise any of a variety of known or future image processing applications. Some examples of known instrument control and image processing applications include the Affymetrix Microarray Suite, and Affymetrix GeneChip Operating Software (hereafter referred to as GCOS) applications. Typically, embodiments of applications 372 may be loaded into system memory 270 and/or memory storage device 281 through one of input devices 240.

Some improved embodiments of applications 372 include executable code being stored in system memory 270, illustrated in FIG. 3 as instrument control and analysis applications executables 372A, of an implementation of server 120.

For example, the described embodiments of applications 372 may include what may be referred to as the Affymetrix command-console software. Embodiments of applications 372 may advantageously provide what is referred to as a modular interface for one or more computers or workstations and one or more servers, as well as one or more instruments. The term "modular" as used herein generally refers to elements that may be integrated to and interact with a core element in order to provide a flexible, updateable, and customizable platform. For example, as will be described in greater detail below applications 372 may comprise a "core" software element enabled to communicate and perform primary functions necessary for any instrument control and image processing application. Such primary functionality may include communication over various network architectures. In the present example, modular software elements, such as for instance plug-in module 376, may be interfaced with the core software element to perform more specific or secondary functions. In particular, the specific or secondary functions may include functions customizable for particular applications desired by user 101. Further, modules integrated with the core software elements may be a single software application such as applications 372.

In the presently described implementation, applications 372 may communicate with and control one or more elements or processes of the one or more servers, one or more workstations, and the one or more instruments. Also, embodiments of server 120 or computer 150 with an implementation of applications 372 stored thereon could be located locally or remotely and communicate with one or more additional servers and/or one or more other computers/workstations or instruments.

In some embodiments, applications 372 may also be enabled to encrypt data such as one or more data files that will be described in greater detail below, where the encrypted data may then be distributed over network 125 to one or more other computers or servers. For example, some embodiments of probe array 140 may be employed for diagnostic purposes where the data may be associated with a patient and a diagnosis of a disease or medical condition. It is desirable in many applications to protect the data using encryption for confidentiality of patient information. In addition, one-way encryption technologies may be employed in situations where access should be limited to only selected parties such as a patient and their physician. In some applications, the one-way encrypted data may be stored in one or more public databases or repositories where even the curator of the database or repository would be unable to associate the data with the user. The described encryption functionality may also have utility in clinical trial applications where it may be desirable to isolate one or more data elements from each other for the purpose of confidentiality and/or removal of experimental biases.

Applications 372 may, in the present implementation, provide one or more interactive graphical user interfaces that allows user 101 to make selections based upon information presented in an embodiment of GUI 246. Those of ordinary skill will recognize that embodiments of GUI 246 may be coded in various language formats such as an HTML, XHTML, XML, javascript, Jscript, or other language known to those of ordinary skill in the art used for the creation of enhancement of "Web Pages" viewable and compatible with internet client 379. As described above with respect to internet client 279, interim client 379 may include various internee browsers such as Microsoft Internet Explorer, Netscape Navigator, Mozilla Firefox, Apple Safari, or other browsers known in the art. Applications of GUI's 246 viewable via one or more interact type browsers may allow user 101 complete remote access to data, management, and registration functions without any other specialized software elements. Applications 372 may provide one or more implementations of interactive GUI's 246 that allow user 101 to select from a variety of options including data selection, experiment parameters, calibration values, and probe array information within the access to data, management, and registration functions.

In some embodiments, applications 372 may be capable of running on operating systems in a non-English format, where applications 372 can accept input from user 101 in various non-English language formats such as French, Spanish, and output information to user 101 in the same or other desired language output. For example, applications 372 may present information to user 101 in various implementations of GUI 246 in a language output desired by user 101, and similarly receive input from user 101 in the desired language. In the present example, applications 372 is internationalized such that it is capable of interpreting the input from user 101 in the desired language where the input is acceptable input with respect to the functions and capabilities of applications 372.

Embodiments of applications 372 also include instrument control features, where the control functions of individual types or specific instruments such as scanner 100, autoloader 110, or fluid handling system 115 may be organized as plug-in type modules to applications 372. For example, each plug-in module may be a separate component such as plug-in module 373 and may provide definition of the instrument control features to applications 372 where each plug-in module 373 is functionally integrated with executables 372A when stored in system memory 370. In the present example, each instrument may have one or more associated embodiments of plug-in module 373 that for instance may be specific to the model of the instrument, revision of instrument firmware or scripts, number and/or configuration of instrument embodiment. Further, multiple embodiments of plug-in module 373 for the same instrument such as scanner 100 may be stored in system memory 370 for use by applications 372, where user 101 may select the desired embodiment of module 373 to employ, or alternatively such a selection of module 373 may be defined by data encoded directly in a machine readable identifier as described below or indirectly via an array file, library files, experiment files and so on.

The instrument control features may include the control of one or more elements of one or more instruments that could, for instance, include elements of a hybridization device, fluid handling system 115, autoloader 110, and scanner 100. The instrument control features may also be capable of receiving information from the one more instruments that could include experiment or instrument status, process steps, or other relevant information. The instrument control features could, for example, be under the control of, or an element of, the interface of applications 372. In some embodiments, a user may input desired control commands and/or receive the instrument control information via one of GUI's 246. Additional examples of instrument control via a GUI or other interface is provided in U.S. patent application Ser. No. 10/764,663 (abandoned), which is hereby incorporated by reference herein in its entirety for all purposes.

Figure 4:
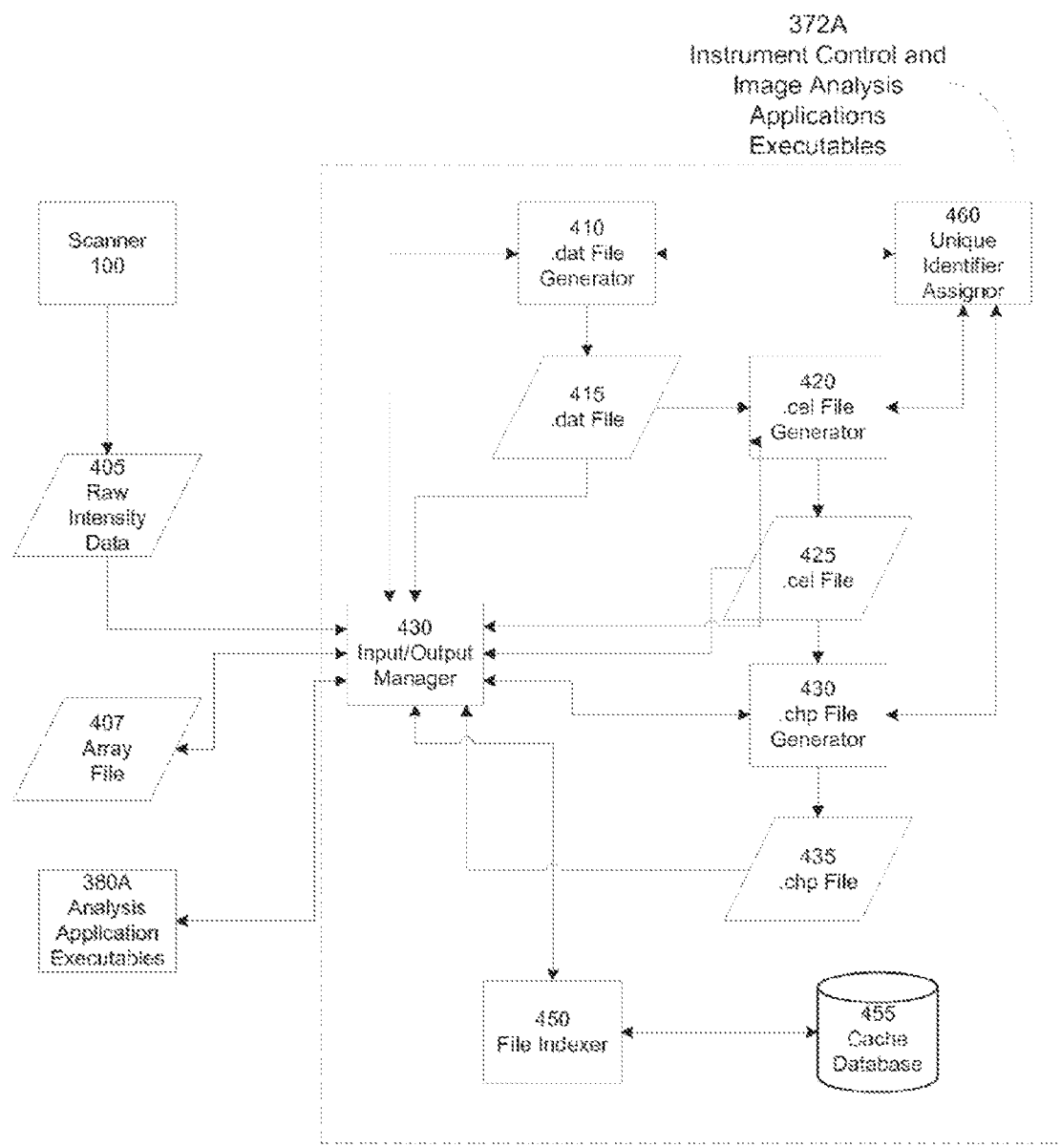
FIG. 4 is a functional block diagram of one embodiment of the instrument control and image analysis application of FIG. 3 comprising an analysis application that receives process image files from the instrument control and image analysis application of FIG. 3 for additional analysis.

In some embodiments, applications 372 may employ what may be referred to as an "array file," represented in FIG. 4 as array file 407, which comprises data employed for various processing functions of images by applications 372 as well as other relevant information. Generally, it is desirable to consolidate elements of data or metadata related to an embodiment of probe array 140, experiment, user, or some combination thereof, to a single file that is not duplicated (e.g. as embodiments of .dat file 415 may be in certain applications), where duplication may sometimes be a source of error. The term "metadata" as used herein generally refers to data about data. It may also be desirable in some embodiments to restrict or prohibit the ability to overwrite data in array file 407. Preferentially, new information may be appended to the file providing the benefit of traceability, and data integrity (e.g. as may be required by some regulatory agencies). For example, array file 407 may be associated with one or more implementations of an embodiment of probe array 140, where array file 407 acts to unify data across a set of probe arrays 140. Array file 407 may be created by applications 372 via a registration process, where user 101 inputs data into applications 372 via one or more of GUI's 246. In the present example, array file 407 may be associated with a custom identifier such as a machine readable identifier that could include identifiers described in greater detail below. Alternatively, applications 372 may create array file 407 and automatically associate array file 407 with a machine readable identifier that identifies an embodiment of probe array 140. Applications 372 may employ various data elements for the creation or update of array file 407 from one or more library files, such as library files 274 or other library files, where the information may be provided by a manufacturer of probe array 140 and define characteristics such as probe location and identity, dimension and positional location, e.g. with respect to some fiducial reference of the active area of probe array 140, various experimental parameters, instrument control parameters, or other types of useful information. In addition, array file 407 may also contain one or more metadata elements that could include one or more of a unique identifier for array file 407, human readable form of a machine readable identifier, or other metadata elements. In addition, the applications 372 may store data, e.g. as metadata, or stored data, that includes sample identifiers, array names, user parameters, event logs that may for instance include a value identifying the number of times an array has been scanned, relationship histories such as for instance the relationship between each .cel file and the one or more .dat files that were employed to generate the .cel file, and other types of data useful in for processing and data management.

For example, user 101 and/or automated data input devices or programs (not shown) may provide data related to the design or conduct of experiments. User 101 may specify an Affymetrix catalogue or custom chip type (a catalog array such as the Mapping 6.0 Array) either by selecting from a predetermined list presented in one or more of GUI's 246 or by scanning a bar code, Radio Frequency Identification (RFID), magnetic strip, or other means of electronic identification related to a chip to read its type. Applications 372 may associate the chip type with various scanning parameters stored in data tables or library files, such as library files 274 of computer 150, including the area of the chip that is to be scanned, the location of chrome elements or other features on the chip used for auto-focusing, the wavelength or intensity/power of excitation light to be used in reading the chip, and so on. Also, applications 372 may encode array files 407 in a binary type format that may minimize the possibility of data corruption. However, applications 372 may be further enabled to export array file 407 in a number of different file formats.

Also, in the same or alternative embodiments, applications 372 may generate or access what may be referred to as a "plate" file. The plate file may encode one or more data elements such as pointers to one or more array files 407, and preferably may include pointers to a plurality of array files 407.

In some embodiments, raw image data is acquired from scanner 100 and operated upon by applications 372 to generate intermediate results. For example, raw intensity data 405 acquired from scanner 100 may be directed to .dat file generator 410 and written to data files (*.dat) such as .dat file 415 that comprises an intensity value for each pixel of data acquired from a scan of an embodiment of probe array 140. In the same or alternative embodiments it may be advantageous to scan sub-areas (that may be referred to as sub-arrays) of probe array 140 where raw intensity data 405 for each sub-area scanned may be written to an individual embodiment of .dat file 415. Continuing with the present example, applications 372 may also include unique identifier assignor 460 that encodes a unique identifier for .dat file 415 as well as a pointer to an associated embodiment of array file 407 as metadata into each .dat file 415 generated. The term "pointer" as used herein generally refers to a programming language datatype, variable, or data object that references another data object, datatype, variable, using a memory address or identifier of the referenced element in a memory storage device such as in system memory 370. In some embodiments the pointers comprise the unique identifiers of the files that are the subject of the pointing, such as for instance the pointer in .dat file 415 described above comprises the unique identifier of array file 407. Additional examples of the generation and image processing of sub-arrays is described in U.S. patent application Ser. No. 11/289,975 (abandoned), which is hereby incorporated by reference herein in its entirety for all purpose.

Also, applications 372 may also include .cel file generator 420 that may produce one or more .cel files 425 (*.cel) by processing each .dat file 415. Alternatively, some embodiments of .cel file generator 420 may produce a single .cel file 425 from processing multiple .dat files 415 such as with the example of processing multiple sub-arrays described above. Similar to .dat file 415 described above each embodiment of .cel file 425 may also include one or more metadata elements. For example, assignor 460 may encode a unique identifier for each .cel file 425 as well as a pointer to an associated array file 407 and/or the one or more .dat files 415 used to produce the .cel file 425.

Each .cel file 425 contains, for each probe feature scanned by scanner 100, a single value representative of the intensities of pixels measured by scanner 100 for that probe. For example, this value may include a measure of the abundance of tagged mRNA's present in the target that hybridized to the corresponding probe. Many such mRNA's may be present in each probe, as a probe on a GENECHIP® probe array may include, for example, millions of oligonucleotides designed to detect the mRNA's. Alternatively, the value may include a measure related to the sequence composition of DNA or other nucleic acid detected by the probes of a GENECHIP probe array. As described above, applications 372 receives image data derived from probe array 140 using scanner 100 and generates .dat file 415 that is then processed to produce .cel intensity file 425, where applications 372 may utilize information from array file 407 in the image processing function. For instance, .cel file generator 420 may perform what is referred to as grid placement on the image data in .dat file 415 using data elements such as dimension information to determine and define the positional location of probe features in the image. Typically, .cel file generator 420 associates what may be referred to as a grid with the image data in a .dat file for the purpose of determining the positional relationship of probe features in the image with the known positions and identities of the probe features. The accurate registration of the grid with the image is important for the accuracy of the information in the resulting .cel file 425. Also, some embodiments of .cel file generator 420 may provide user 101 with a graphical representation of a grid aligned to image data from a selected .dat file in an implementation of GUI 246, and further enable user 101 to manually refine the position of the grid placement using methods commonly employed such as placing a cursor over the grid, selecting such as by holding down a button on a mouse, and dragging the grid to a preferred positional relationship with the image. Examples of grid registration and methods of positional refinement are described in U.S. Pat. Nos. 6,090,555, 6,611,767, 6,829,376 and 7,130,458, and U.S. patent application Ser. No. 10/391,882 (abandoned), each of which is hereby incorporated by reference herein in its entirety for all purposes.

As noted, another file that may be generated by applications 372 is .chp file 435 using .chp file generator 430. For example, each .chp file 435, which may alternately also be a .cychp or .cnchp file, is derived from analysis of .cel file 425 combined in some cases with information derived from array file 407, other lab data and/or library files 274 that specify details regarding the sequences and locations of probes and controls. The resulting data stored in .chp file 435 includes degrees of hybridization, absolute and/or differential (over two or more experiments) expression, genotype comparisons, detection of polymorphisms and mutations, and other analytical results, as explained in further detail below. There may be at least two different kinds of .chp files. For instance, a .cnchp file will contain output data which is pertinent to gene copy number state, including gain segments and loss segments, as defined in further detail below. Alternatively, the .chp file may be a .cychp file, which is defined to contain data pertinent to genotype-based results or "base calling" data, and may further contain information pertinent LOH, LCSH, allele identity and allele peak data.

In some alternative embodiments, user 101 may prefer to employ different applications to further process or perform higher level/specialized analysis such as analysis application 380. Various embodiments of analysis application 380 may exist such as applications developed by the manufacturer for specialized embodiments of probe array 140, commercial third party software applications, open source applications, or other applications known in the art for specific analysis or high level analysis of data from probe arrays 140. Applications 372 may be enabled to export .cel files 425, .dat files 415, or other files to analysis application 380 or allow access to such files on computer 150 by analysis application 380. Such functionality may be enabled by one or more modules as described above with respect to plug-in module 373.

Additional examples of .cel and .chp files are described with respect to the Affymetrix GENECHIP® Operating Software or Affymetrix Microarray Suite (as described, for example, in U.S. Pat. No. 7,031,846 or U.S. patent application Ser. No. 10/764,663 (abandoned), both of which are hereby incorporated herein by reference in their entireties for all purposes). For convenience, the term "file" often is used herein to refer to data generated or used by applications 372 and executable counterparts of other applications such as analysis application 380, where the data is written according a format such as the described .dat, .cel, and .chp (including .cychp and .cnchp) formats. Further, the data files may also be used as input for applications 372 or other software capable of reading the format of the file.

Some embodiments of applications 372 may be enabled to store and manage data stored in a file format or file based system. For example, a file based system may provide a high degree of flexibility over Database type storage formats where the database formats may require knowledge of a particular data model or organization of data in order to work effectively. In the present example, file based systems are not bound by such formatting constraints, thereby allowing greater flexibility to user 101 and developers of third party software elements. For instance, embodiments of application 380 enabled to process files generated by applications 372. In the same or alternative examples, user 101 and/or the third party developers may employ what are referred to as software development kits that enable programmatic access into file formats, or the structure of applications 372. Therefore, other software applications may integrate with and seamlessly add functionally to or utilize data from applications 372 that provides user 101 with a wide range of application and processing capability. Additional examples of software development kits associated with software or data related to probe arrays are described in U.S. Pat. Nos. 6,954,699 and 7,451,047, and U.S. patent application Ser. No. 10/764,663 (abandoned), all of which are hereby incorporated by reference herein in its entirety for all purposes.

Some embodiments of applications 372 may employ a system of file management that employs a method or data structure that utilizes a unique identifier associated with each file and a system of pointers within files that identify relationships between the files. File-based systems have advantages over database type methods of storing and managing probe array information. For instance, a file based system opens the results and data produced by the software platform to use by third party software. Additionally, the file based system allows users flexibility to organize and store data in a manner that is preferred by the users and more amenable to their work flow and data management.

Embodiments of the unique identifier are independent of file names or other commonly used identifiers. One advantage of associating a unique identifier with each file is that it allows for the changing of file names by user 101, there the unique identifier still allows the file to be organized in a particular relationship with other files independent of the file name. For example, some management systems employ the name of a particular file to track and identify the file such that the relationship with a first file to one or more other files is dependent upon the name of the first file. In the present example, if the name of the first file is changed or modified in any way, the relationships to other the one or more other files may be lost. On the other hand, utilizing a unique identifier embedded as metadata within the file may be protected from overwriting and thus the integrity of relationships that depend upon the identifier is more stable.

Methods of generating unique identifiers may be accomplished in a variety of ways and can include a variety of non-random elements such as one or more of time based identifiers, machine or system identifiers, network identifiers, laboratory identifiers, user identifiers, identifiers particular to the experiment or application, or site based identifiers. Other elements of a unique identifier may also include one or more randomly generated identifiers, or other types of random and non-random identifiers known to those of ordinary skill in the related art. Those of ordinary skill in the art will appreciate that a unique identifier may comprise one or more of the elements described above or any combination thereof. For example, applications 372 may employ algorithms that generate unique identifiers comprising a plurality of elements arranged in a particular order. The elements may include elements in the following arrangement: Time—Network Address—Random—Random. In the present example, the arrangement of elements may comprise a string of characters and the time element may include a reference to system time (e.g. computer system such as computer 150), Greenwich Mean Time, or other standard time reference and the random elements may comprise strings of random characters such as numbers, letters, symbols, or other commonly employed characters.

In the presently described embodiments, the relationship between files may be arranged in a variety of ways. In one embodiment, applications 372 employs a file management data structure organized in a hierarchical-like format such as for instance a tree-like hierarchical structure where a primary file(s) comprises the "root" of the tree structure and subsequent tiers of files represent dependencies of each file on the data in the file from the tier or tiers above. Typically, the tiers may be viewed as having a "parent-child" type relationship where each parent file in a respective tier may have one or more child files in the tier below such as for instance each .dat file may be the parent to one or more .cel files in the tier below. Advantageously, the described file management structure provides user 101 with complete downstream traceability of files derived from information in the root file and tiers above. The present example of a hierarchical structure is used for the purposes of explanation of the nature of relationships between files and should not be confused with other types of tree-like data structure known in the art. For example, the .dat file may be considered the root file for all subsequent downstream files where a second tier comprises one or more .cel files derived from the .dat file, and a third tier may comprise one or more .chp files derived from each .cel file, where a file in each respective tier comprises a pointer to the child file in the tier below, and all files comprise a reference to the unique identifier associated with a common array file. In the present example, one or more .cel files may be processed from a single .dat file where each .dat file includes a pointer to the unique identifier of the .cel file. Further, one or more .chp files, such as a .cychp file or .cnchp file, for example, may be generated from each .cel file where each .chp includes a pointer o the unique identifier of the .cel file from which it was generated, and in some embodiments may also include a pointer to the .dat and/or array file from which the .cel file was generated.

Additionally, embodiments of applications 372 may include file indexer 450 that utilizes and maintains a small database (e.g. maintains a minimal amount of information) for the purpose of searching and identifying files or specific data elements of interest. Such a database may include cache database 455 that comprises data that duplicates data computed earlier and/or stored elsewhere. For example, it may be advantageous to provide cache database 455 for use in searching for files or specific elements contained within the files such as the .dat, .cel, .chp, and other similar array files. In the present example, cache database 455 comprises the metadata of each file organized in the database according to a preferred data model. Additional data stored in cache database 455 for each file could also include memory addresses, current file names, file size, date/time stamps, electro signatures, or other information that does not include probe array data such as raw or processed intensity values. Such a database provides an advantage because the alternative is to open each of the files until the desired information is obtained. In some embodiments, indexer 450 comprises a search engine to find various files or specific data elements within the database. Also user 101 may employ an implementation of GUI 246 to create search queries for files or specific data elements where input/output manager 430 may provide GUI 246 and direct search queries to indexer 450.

Analysis Application 380: Analysis Application 380 of the invention may comprise a probe array analysis software application, and particularly analysis applications specialized for use with embodiments of probe array 140 designed for genotyping applications. Such genotyping analysis applications may be found in U.S. patent application Ser. No. 10/657,481 (abandoned), Ser. No. 10/986,963 (abandoned) and Ser. No. 11/157,768 (U.S. Patent Application Publication No. 20050287575, abandoned); each of which is hereby incorporated by reference herein in its entirety for all purposes. Typically, embodiments of applications 380 may be loaded into system memory 270 and/or memory storage device 281 through one of input devices 240.

Some embodiments of applications 380 include executable code being stored in system memory 270, illustrated in FIG. 3 as instrument control and analysis applications executables 380A. As illustrated in FIG. 4, Analysis Application Executables 380A may receive one or more files from input/output manager 430. For example, Analysis Application Executables 380A may be capable of specialized analysis of processed data, such as the data in .cel file 425. In the present example, user 101 may desire to process data associated with a plurality of implementations of probe array 140 and therefore Analysis Application Executables 380A would receive a .cel file 425 for processed from each probe array. In the present example, manager 430 forwards the appropriate files in response to queries or requests from Analysis Application Executables 380A.

Analysis Application Executables 380A may receive each of .cel files 425 and analyze the data using one or more algorithms to determine a genotype call for each SNP represented by a probe set (e.g. set of one or more probes that interrogate the same target), and one or more measure of quality or confidence associated with the genotype call.

Analysis Application Executables 380A may in preferred applications analyze all .cel files 425 in parallel, where higher quality results may be obtained using the combination of data elements from each .cel file 425. Initially, Analysis Application Executables 380A will "normalize" the intensity data from each of files 425. The term "normalize" as used herein generally refers to performing a process of comparing and adjusting intensity values in each .cel file to a same scale or range such that the intensity values from each of the files is comparable to one another. Analysis Application Executables 380A may employ a variety of normalization methods that may include but are not limited to quantile normalization, or sketch normalization, or other such normalization methods as described in more detail below.

In some embodiments, Analysis Application Executables 380A may also determine an initial assignment for each SNP genotype using a variety of methods. In some embodiments, Analysis Application Executables 380A may perform this function in parallel to the normalization described above. For example, Analysis Application Executables 380A may employ what is referred to as Dynamic Modeling (DM) methods and algorithms to make the initial assignment of genotype, where the intensity values are fit to models, and the genotype is determined by the best fit of the data for each SNP to a particular genotype model. Additional examples of dynamic modeling algorithms are described in U.S. patent application Ser. No. 10/657,481 (abandoned), Ser. No. 10/986,963 (abandoned), and Ser. No. 11/157,768 (abandoned), the contents of all of which are incorporated by reference.

In a typical method of this type, Analysis Application Executables 380A then identifies a minimum number of instances of each of the three genotype calls (e.g. AA, AB, BB) for the initial assignments and uses these identified instances to estimate the prior distribution on typical cluster centers and variance-covariance matrices. Next, Analysis Application Executables 380A may process the data associated with each SNP by combining the cluster centers and variances with the data employing what is referred to as a Bayesian method (see, "Bayesian Data Analysis," by Andrew Gelman, John B. Carlin, Hal S. Stern, and Donald B. Rubin, $2^{nd}$ edition, Boca Raton, Fla., Chapman & Hall/CRC Press, 2004, hereby incorporated by reference in its entirety for all purposes) to derive a posterior estimate of cluster centers and variances. Lastly, Analysis Application Executables 380A assigns a genotype and confidence score for each SNP according to what is referred to as its Mahalanobis distance (distance resealed by the variance & covariance) from the three cluster centers.

Analysis Application Executables 380A may return the genotype values to Instrument control and image processing applications 372 for processing into a file format or alternatively Analysis Application Executables 380A may generate a file. Some or all of the SNP results including the genotype calls and/or confidence values may also be presented to user 101 in one or more GUIs 246, as described in further detail by additional embodiments of the invention.

IV. Specific Embodiments of the Invention—Software Application

The invention disclosed herein pertains to software applications which aid in the identification and display of large amounts of complex genetic information, such as copy number variations. As explained in the process and systems described above, detection, by scanning of the intensities of fluorescent signals on a probe array, typically generates a data file containing signal intensity data, referred to as a ".cel" file. The .cel files may be converted into .cnchp or .cychp files (types of .chp files), as explained above, which represent normalized intensity values obtained from the probe array during a hybridization experiment. The values are normalized by obtaining a ratio of the value with respect to a baseline reference set of normal samples. Files such as .cnchp flies may be generated using many different gene copy number algorithm outputs, including, for instance, an algorithm utilizing a $\log_2$ ratio relative to a baseline and a Copy Number state (CNState) calculated by Hidden Markov Model (HMM) analysis of the $\log_2$ ratios into Copy Number States. As explained above, such data provide information about markers, SNP sequences and/or copy number information, concerning genetic content within the tested or hybridized sample.

An exemplary flow of the data analysis for the disclosed system and process may proceed as follows. First, intensity values may be obtained from the probe array tested with the experimental sample and exported into a .dat file (or multiple such files). Second, the .dat file may be converted to a .cel file as explained above. Third, an HMM algorithm, or similar mathematical analysis algorithm, may be employed by the software's APT system to convert the data into normalized data, exported as a .cychp file, or a .cnchp file, for instance. These .cychp and/or .cnchp data files contain information utilized by the software application browser to display the information in multiple colors and a variety of windows, showing various segments of genomic sequences information to the user for visual inspection and analysis. Within the software program, the user may then alter or change various parameter settings for the segments, define specific CytoRegions and/or apply various filters, as well as modify the data further by smoothing and joining the segments. Various filters may be applied by the user, as explained in further detail below, wherein one set of filter parameters may be applied to the entire genome, and/or a different set of user-defined filtering parameters may be applied to just the CytoRegions.

Embodiments of the user-provided application described above include computer software which displays to the user the genetic data obtained from the experiments. The data is displayed by the software in various manners on a computer screen or other visual media such as a visual projector, screen, and/or board. The software application disclosed herein enables a user to compare data obtained from a microarray, for instance, in the form of a .cel file, to another .cel file or to a file an .rmf file. The .rmf file is like a .cel file but contains microarray intensity values for multiple test samples, not just for a single test or reference sample. The display of the data may be in color and may be interactive, allowing the user to define various functionalities and various segments of genome being investigated by the experiment. For instance, the application may contain programming that allows the display of a map of the entire genome of the animal, bacteria, plant or other entity of interest. The genome may be human, mouse, insect, plant, bacterial or any other type of genome. The genetic map displayed to the user may be in color and particularly may make use of various colors to signify different functionalities or characteristics of the genetic data. Furthermore, the application may enable a user to interface directly with the genomic map obtained from the data, which may display, for instance, the identities of the various SNP sequences identified by the genetic experiment(s). The genetic map may be depicted in the form of chromosomes, or shapes which mimic or reflect traditional depictions of chromosome shapes as seen by, for instance, a cytogenetecist examining chromosomes through a microscope.

The Affymetrix Chromosome Analysis Suite (ChAS, available from Affymetrix, Inc., Santa Clara, Calif.) is a non-limiting example of the invention. The various possible features that may be presented in the software program display are disclosed in exemplary embodiments in the ChAS software. The ChAS User Manual, which is available and freely downloadable in .pdf form from the Affymetrix website, is specifically incorporated herein by reference in its entirety for all purposes. The ChAS is an example of the manner in which differential filtering may be implemented using various selected computer software languages, visual depictions and user interface/interaction menus. While this example provides a single embodiment of the presently disclosed invention, it is understood that many minor changes and variations may be made; for example, the selection of an alternate coding language, the choice of windows to be displayed or not displayed, the color selections, variation of demarcations and avatars, for example, known to one of skill in the art. The present disclosure is non-limiting in that it is meant to capture, and contemplates all of these variations and changes that may be made to the invention such that the user may be provided with the tools necessary to implement differential filtering of genetic data as presently disclosed hereinbelow.

The software application of the invention, which depicts the genetic information obtained from various hybridization experiments, enables the user to select various segments of the genome or chromosomes investigated by the experiment. Such segments of chromosomes may be selected based on several user-defined criteria. These segments may be selected by the user and displayed in a distinguishable and meaningful manner to the user via the software application browser using a segmentation process.

Figure 5:
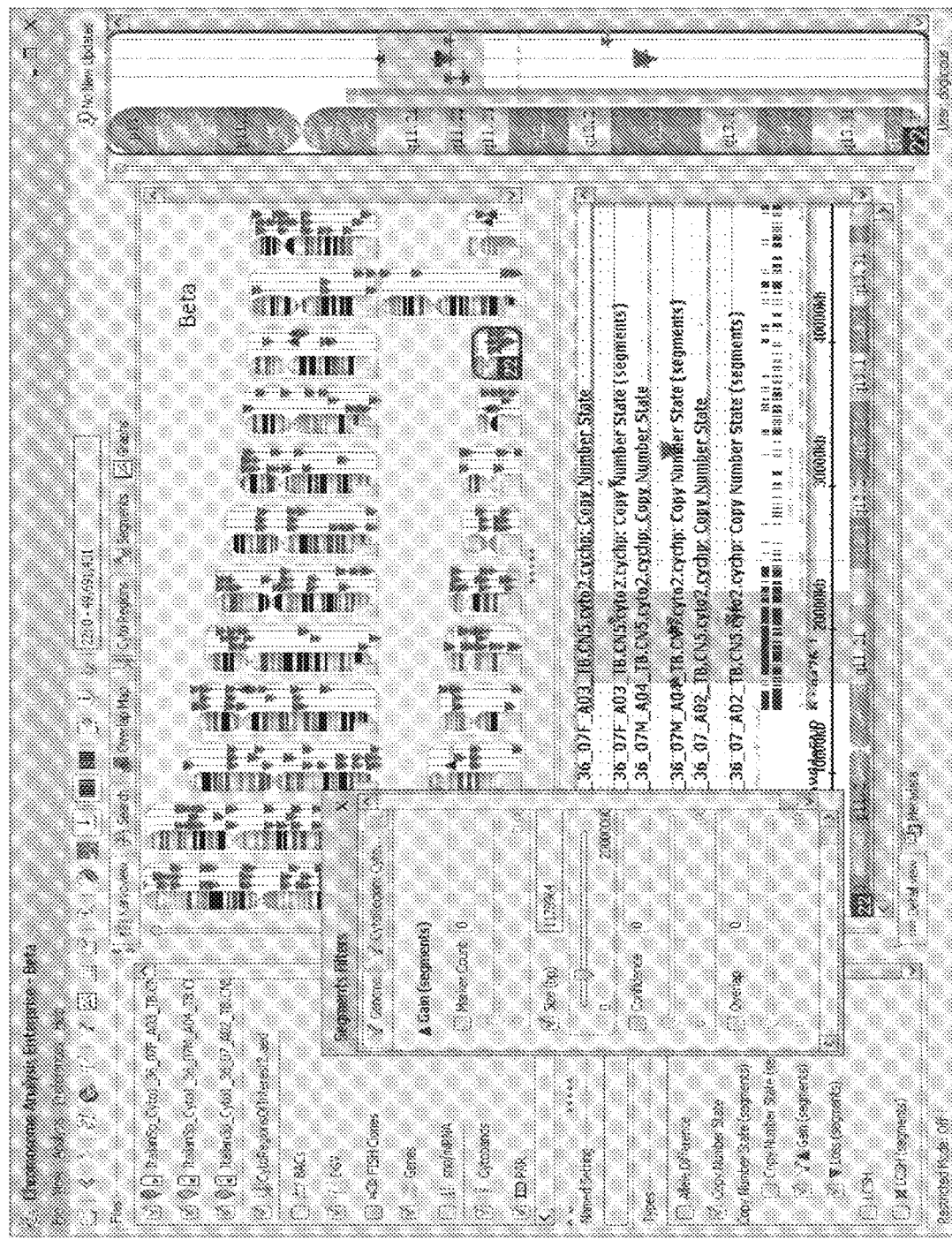
FIG. 5 is an exemplary depiction of the display or graphical user interface.

The user may be prompted by the software program or by the goals of the experiment, to select one or more chromosomes of particular interest to the user, which are depicted on the computer screen or other visualization device. The selected chromosome or chromosomes may be depicted visually in one window on the computer screen, while other data are separately displayed in other windows on the screen, in a windows-based computer software application/browser environment (operating system) of the present software application. Operating systems compatible with the presently described software application may include, but are not limited to, Windows, Unix, Mac, Linux, Unisys, Solaris, GNU, Pascal and the like. Multiple windows may be displayed simultaneously, with each window containing subsets of information and/or data depicted to the user for visual inspection and analysis. The data displayed by each window may be custom manipulated by the user such that only the data desired or most important to the user is shown, or is highlighted in a meaningful manner. One such window may display a segment of the chromosome selected by the user based on the aforementioned variables determined by the user. For instance, the display depicted in FIG. 5 is illustrative of the presentation of the presently described software application. Multiple chromosomes are depicted in a first window (upper middle window), with the single selected chromosome displayed in a second window (window on the far right of the screen). A third window displays a further detailed depiction of specific segments of DNA (lower middle window) selected by the user using the user interface available in the software (topmost depicted window entitled "Segment Filters"). Further windows display data and variables which modify the data as selected by the user (upper left corner of the display of FIG. 5).

In some embodiments, the segmentation process functionalized by the software application is performed using a $\log_2$ ratio of data. For instance, if a .cel file is accessed by the software application for display, the .cel file may contain intensity values corresponding to various features on the probe array. The intensity values are empirically determined by a scanning laser which detects signals from, for instance, the hybridization of a labeled gene sample to the probe array, as explained above. These intensity values are compared in silico to the values in a reference, which may be a reference model, e.g. an ideal model of the predicted or expected or average outcome of the experiment, or it may be another .cel data file or .rmf file. This comparison is made by determining a ratio of the experimentally determined intensity values in a .cel file with the reference. Such a ratio is generated in silico by the software application as a $\log_2$ ratio.

Thus, the $\log_2$ ratio is the normalized intensity data obtained from the probe array. This ratio also represents the copy number of the experimental genetic material represented by the probes on a probe by probe localization basis. In other words, the ratio value generated by the software application represents the number of copies of a given SNP or other non-polymorphic marker, detected within the experimental gene sample, with respect to the reference. In this manner, the user may obtain what is commonly referred to as the copy number of a gene or SNP or marker.

Such information or data may be displayed in many different ways to the user in a user-defined software application interface, as presently disclosed. For instance, the software application may manipulate the data as explained above and the resultant information be displayed as specific "segments" of the genome. These segments of the genome may be defined or refined by entering various values for various parameters by the user, and thus displayed to the user by the software program, or not displayed, according to the user preferences.

A "segment," as previously discussed, is a visual or tabular representation of a biological or other type of event in genetic material. Segments are derived from discrete data points in linear genomic space by examining the values of contiguous discrete data points, especially those data points which diverge in copy number value, or in some other genetic characteristic, from a reference "normal" data value for the selected region of the genome. These values are obtained directly from the probe array as intensity values indicative to the degree of hybridization of a labeled test sample to the probe array. Hybridization, or lack thereof, of the test sample genetic material to the probe array is indicative of the presence, or of the absence, of a particular genetic sequence, or SNP, or the number of copies of said genetic sequences, or other characteristics of the sequence. Segment boundaries can be comprised of the coordinate data from, at, or immediately adjacent to, two or more such discrete data points. Segments are defined by a start marker and an end marker and are each a discrete size, which are typically measured in nucleotide base pairs. Segments may also be called genetic segments or data segments. Color may be used or various icons may be displayed by the software of the invention, to indicate the presence and/or borders of a segment.

Further, segments which have been smoothed or joined, e.g. those data regions which have been manipulated by the smoothing or joining process, may be further identified by the presently disclosed software programs using various colors and/or icons denoting smoothing or joining. For instance, segments which have been smoothed and/or joined may be indicated by a blue check mark in the smoothed/joined column of the Segments table, as explained in more detail below. Additionally, in the Segments tab also described herein, the software may optionally provide the user with a button or other device which allows the user to indicate or highlight various user-selected segments. An additional entry by the user, for instance by clicking on a symbol provided within the same Segments tab, will provide the user with the summation or total of all segments thus highlighted. That is, the software provides the user with the capability of determining the total sum of the number of kilobases of DNA highlighted by the user by the simple click of an optional button within the software. Furthermore, in the Segments window, the software may optionally provide for the user a column (within the data view) in which the user may freely enter notes or other text as the user so desires. Thus, offering even further flexibility and customization, the software allows the user to enter various notes and thoughts and other, perhaps identifying, information concerning the specific segment indicated in the previous columns, into an optional "free form" column provided by the software. All such comments and segment identifiers in tabular form or other format, may then be exported in pdf format for efficient printing and/or image capture and display in other fixed forms, i.e. as in paper handouts or papers which can then be incorporated into laboratory notebooks and the like.

One type of genetic characteristic or information obtainable by the system and processes described above is the genetic copy number state. Copy Number State (CNState) values are typically determined in series for each chromosome within the genome of the experimental genetic sample to find segments where chromosomal material has incurred a gain or loss of genetic material. Such gains and losses of genetic material may then be displayed as a segment by the software program, and further defined or refined by the user. Other processes may be involved in defining segments, such as smoothing multiple aberrations into a single segment or joining segments over normal data to make a single segment out of multiple initial segments, as explained above concerning smoothing and joining.

In one embodiment of the present invention, the user may input into the computer precise values of CN State to be smoothed or joined. That is, where a user wishes to smooth or join various segments displayed by the computer, the user is allowed to input into the computer the exact values of CN State to be smoothed or joined over the segment being viewed. These values could be entered into the computer to include mosaicism, or non-whole-integer copy numbers. In an extreme case, all mosaicism may be removed from view by entering into the computer various integer parameters instructing that only whole integer CN states be segmented and displayed and those which are not whole numbers (indicating mosaicism) be joined or smoothed with the surrounding CN state of the surrounding segment. This will allow for the enhancement of the size of various segments despite various noise that may occur in the data. The present embodiment offers added flexibility and robustness to the user allowing customization of all states of the smoothing and joining features across any viewable segments on display.

Segments may also be defined by areas of perceived or detected loss of heterozygosity (LOH) or LCSH, and/or may be displayed to be indicative of areas of non-integer CNState, e.g. copy number mosaicism. These are areas where a mixture of samples provide data relating to a specific chromosomal region which varies in integer copy number between the two admixed samples. This is also known as "mosaicism," e.g. a genetic phenomenon wherein the determined copy number of the genetic marker is not a near a whole integer, but rather is between two whole integers.

Segment filtering parameters selected by the user may be used to depict and generate genetic maps of mosaicism as it occurs in admixed experimental genetic samples. The user may be able to enter values or specific definitions of parameters within the software application that determine the nominal values indicative of LOH, LCSH, mosaicism and other such genetic characteristics. Other parameter values may be pre-set by the software application upon installation so that the user need not access or modify those values.

By way of further explanation, the software application may accept .cnchp files as input data, as described above, and generate a segment report, such as a user might expect from a Segment Reporting Tool. The software program identifies and summarizes, for instance, segments that are not equal to a normal Copy Number State of 2. The software may include variables which may be set by the user or pre-set by the software, such as segment size, segment start and stop positions, the number of interrogating markers, e.g. genetic markers being used for purposes of analysis, used to identify the segment, density of markers, and an estimate of the percentage of reported population CNVs within the segment based on external database information, among other possible variables. The presently disclosed software application enables each segment to be visualized as a whole genome "karyoview" in one of the displayed windows, identifying gains and losses across the entire genome tested by the probe array. Users may then analyze the segment data, chromosome by chromosome, as identified by the software in the entered .cnchp data file.

The user may apply various differential filters to the data, as depicted in a visually distinct manner by the software of the invention. The user may apply different user-selected parameter value to conceal or highlight various segments of data that do not meet the requirements set by the user. Examples of such parameters may include, but are not limited to, marker count, length, and confidence value. Filtering may be enabled by the software to be performed "on the fly," which means that the selected chromosomal regions which lie outside of the user-entered parameters may be filtered out, e.g. either appear or disappear or change in appearance in some marked manner, immediately upon the entry of the parameter values by the user. The differential filters entered by the user and depicted by the software may be applied to all segment data in all windows simultaneously. In other words, the parameters entered by the user are reflected in all displayed windows simultaneously, or instantaneously, or nearly instantaneously, as the user is entering the filter parameters into the software-provided dialogue box for such purpose.

The user may also apply different filter values (parameter values) to additional subsets of chromosomal data, e.g. CytoRegions, within the selected segment or across many segments or across all segments depicted by the software application of the invention. These CytoRegions may be depicted differently than the rest of the displayed segments. The user may select multiple, different CytoRegions and apply multiple different filtering parameters all within a single displayed segment, all of which are depicted nearly instantaneously as the user sets the filtration parameters. In other words, a feature of the presently disclosed software application, called CytoRegions, allows the user to visualize areas of special interest and apply different segment filtering thresholds on those selected areas of special interest, as compared to those applied in the rest of the genome view, thus generating an in silico Custom Array.

As a non-limiting example of the windows discussed above, the viewable windows displayed by the computer display device may include the following types of windows: a files list, a data types list, an upper pane to the display area, and a lower pane of the display area, and a selected chromosome view. (See, for instance, FIG. 6). There may also be depicted other features at other locations of the screen, for example a menu bar and a tool bar at the very top of the screen, and a status bar at the bottom of the screen. The arrangement and selection of these various features may be varied innumerable ways known by one of skill in the art of software programming.

The display area is where various segments, which comply with the user-entered filter settings, are displayed. This area may include .cychp and .cnchp graphical data, segments, CytoRegions and other reference annotations or data tracks.

Figure 7:
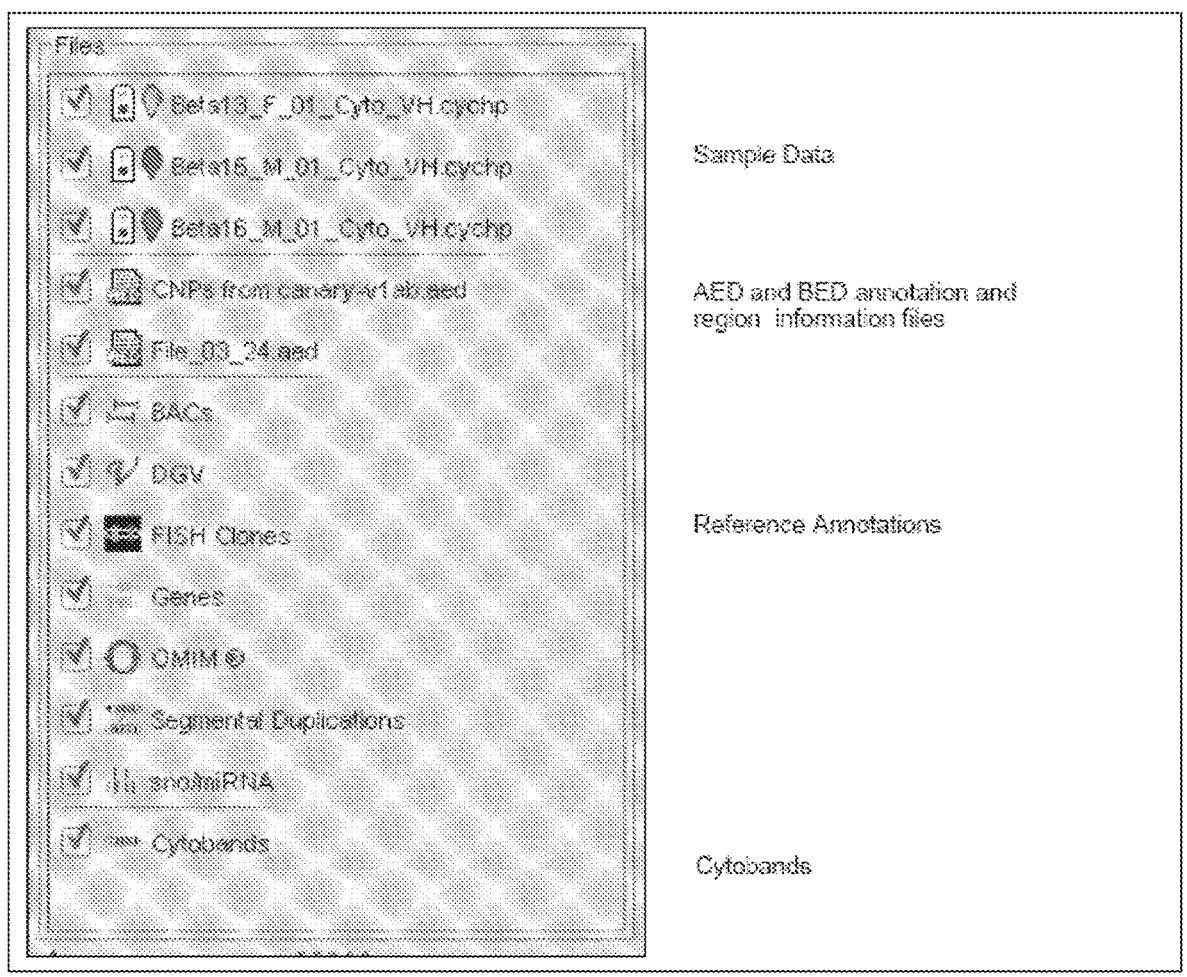
FIG. 7 is an exemplary depiction of an optional files list window.

The files list window may include different sources of data and annotations which are loaded into the software application by the user or included in the software application. FIG. 7 is an exemplary embodiment depicting one possible files list window. This example provides sample data files depicted at the top, AED and BED annotation and region information files, reference annotation files (available on the internet on-line at various locations) and cytobands. A cytoband or cytogenetic band is a subregion of a chromosome which is visible microscopically after special staining is applied to a chromosome sample by a cytogeneticist. Various colored informational avatars may be presented before or after file names. These avatars may be used to show the color that other windows use to display various data files which may be, for example, indications that the data file does not meet with user-defined quality control parameters. Other avatars may be added as needed to provide additional information to the user displayed on the screen. Region information files may be of many varieties, including files such as CytoRegion files or overlap map files. Furthermore, the user may indicate through use of the mouse and by clicking on various option windows within the software, a specific color for their annotated AED and BED files. The software can accept such user-annotated AED and BED files and once loaded, the user can indicate the color in which the software is to display the information in these files for further customization of the display of genetic information. The software may also be capable of uploading and displaying various other user-provided reference annotation files.

Figure 6:
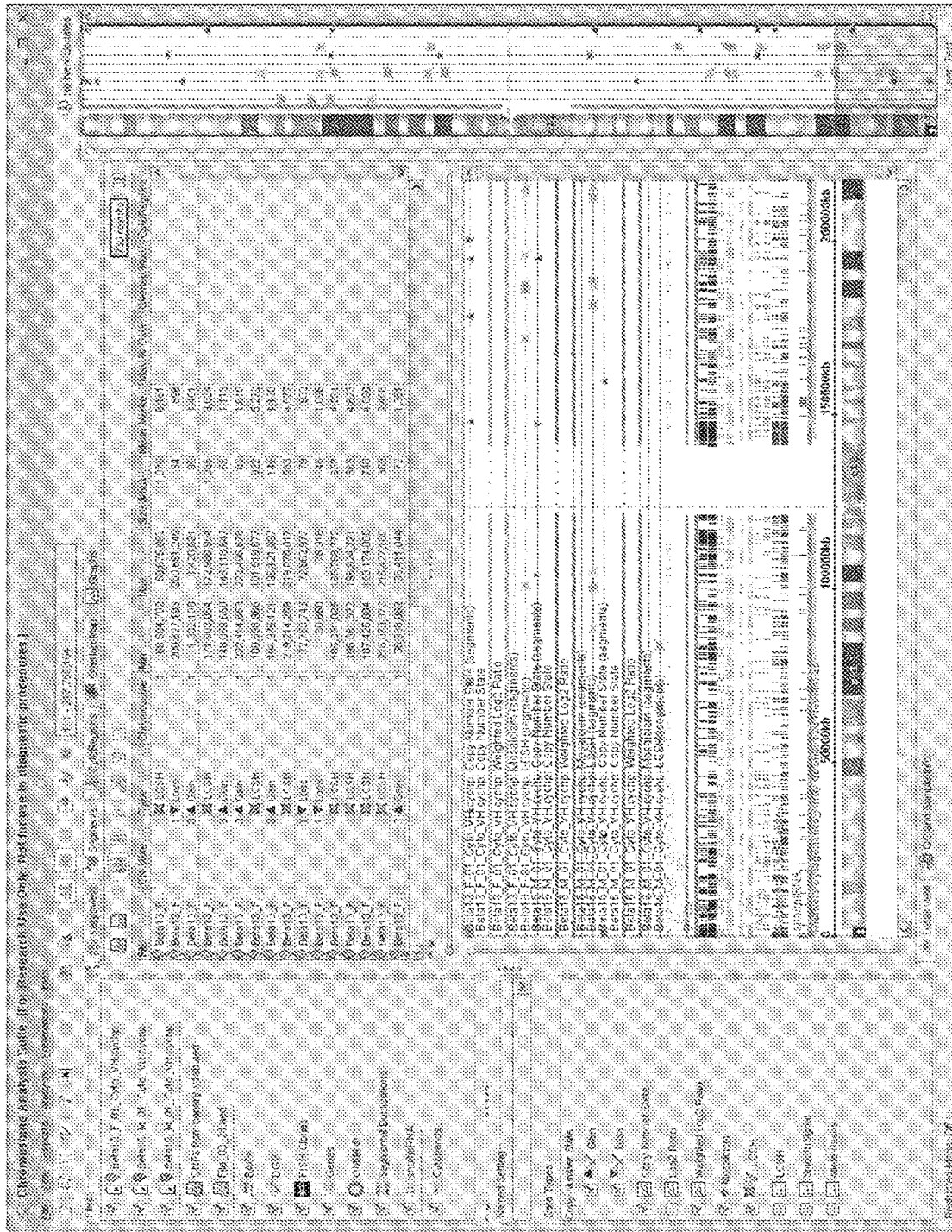
FIG. 6 is another exemplary depiction of the various optional windows which may be displayed by the graphical user interface portion.
Figure 8:
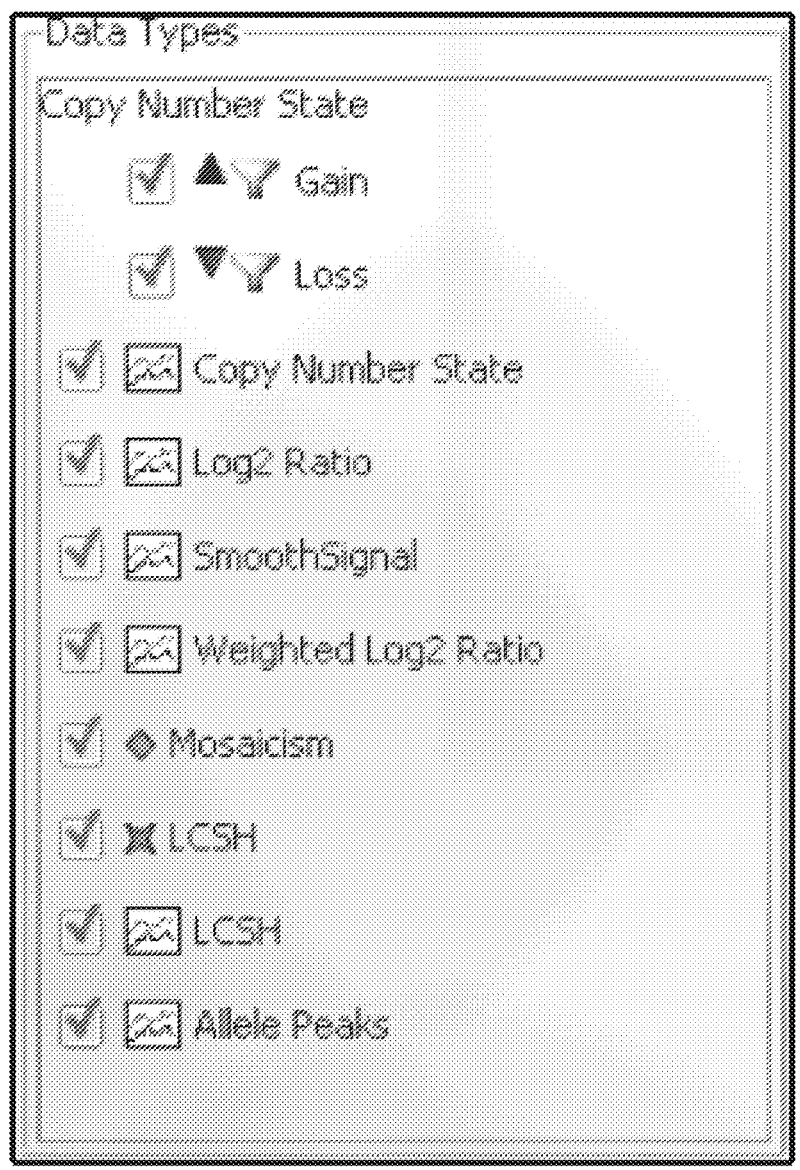
FIG. 8 is an exemplary depiction of an optional window which displays the various types of data that may be displayed in the karyoview window, selected chromosome view and detailed view windows.

Another window which may be made available and displayed to the user is the data types list, such as depicted in the lower left corner of FIG. 6. This optional window, shown again in FIG. 8, displays the various types of data that may be displayed in the karyoview window, the selected chromosome view and the detailed view windows. The types of data able to be displayed may vary depending on the identity of the sample and the sample data available to the software application. As a non-limiting example, the types of data may include CNS gain or loss, CNS, $log_2$ ratio, weighted $log_2$ ratio, mosaicism, LCSH, allele peaks, and other algorithm-based filters that may be applied and adjusted by the user.

Various optional "drop-down" menu windows may also be provided by the software program described herein and made available on the display to the user. Such menus, upon the user selecting them by keyboard operation or mouse action, may appear on the display device, be expanded, and be provided to the user with additional options which may be selected/deselected by the user. The options may include, for instance, an option to select and adjust various segment filter parameters, overlap map filter parameters, and the like. Drop-down menus may allow the user to additionally select the types of data to be displayed.

Figure 9:
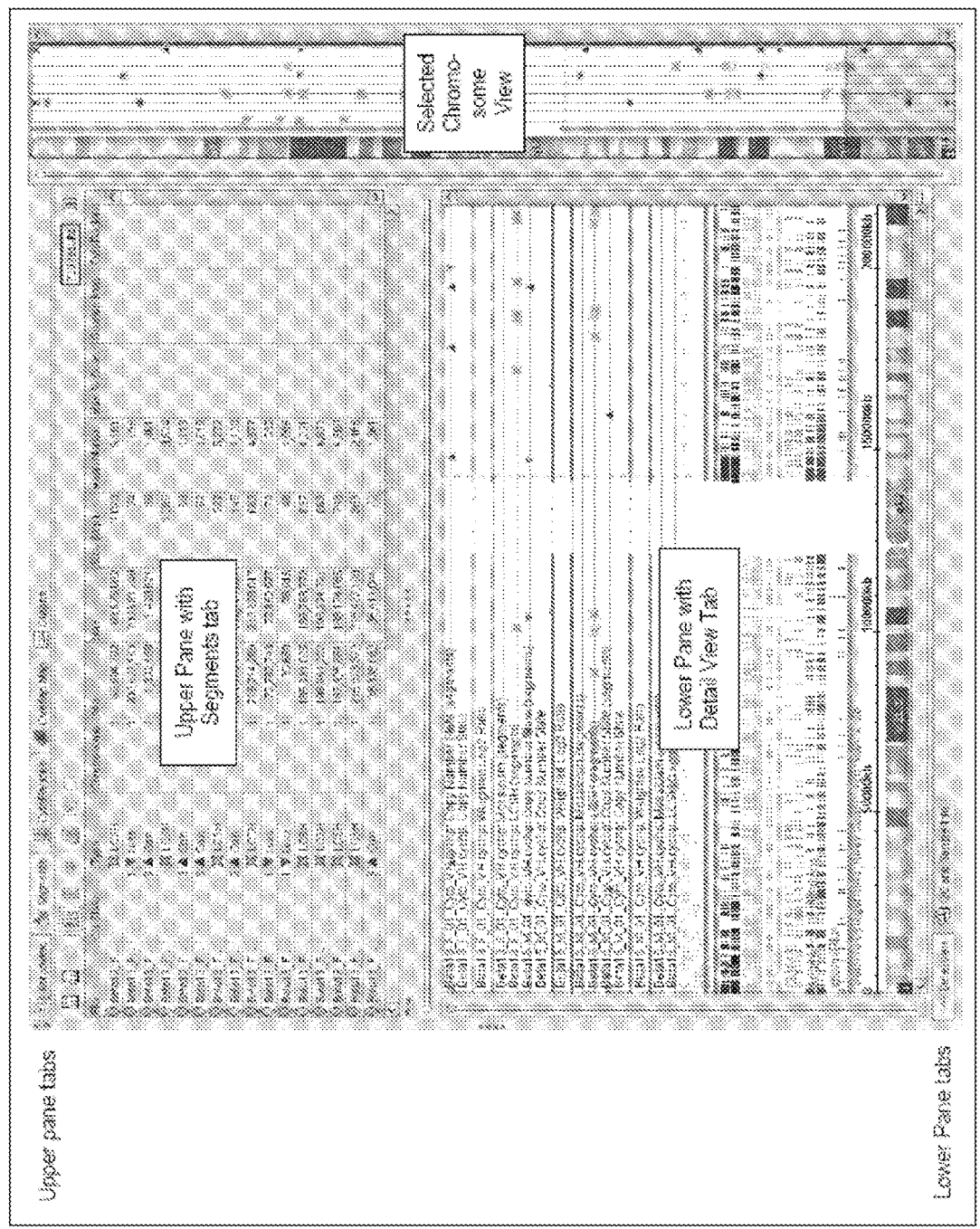
FIG. 9 is an exemplary depiction of an optional window described as the Display Area window.

FIG. 9 depicts in more detail the Display Area window. This additional optional window may be provided by the software program and divided into several different sub-windows, each arranged according to the user's preferences. For instance, there may be depicted an upper window, as in FIG. 9, which provides information about segment data. There may also be a lower window that provides a detailed view of annotation tracks or other data. Additionally, there may be a third window displaying the selected chromosome in detail. Other wind may be added as needed or desired, displaying different aspects of the data and/or chromosome or genetic region of interest to the user.

A non-limiting example of such a Display Area may include an upper pane that provides a karyoview tab which displays selected segment types for selected sample files for all chromosomes, as depicted in FIG. 9. A segments tab which displays a list of the detected segments in the selected sample files may also optionally be provided and displayed to the user. Furthermore, a CytoRegions tab which allows the user to display in the window a list of the regions in the AED or BED or reference annotation files selected by the user as the CytoRegions may optionally be provided and displayed to the user. This optional CytoRegions tab may include information on detected segments which lie in, around or near the user-defined CytoRegions. There may also optionally be included an overlap map tab provided by the software described herein, which when selected by the user, would display in this area of the Display Area a list of regions in the AED/BED/Reference Annotation file that are selected as the overlap map, which may include information on detected segments that are overlapped by overlap map items.

Additionally, there may optionally be provided to the user in the upper window of the Display Area a graphs tab, which when selected could depict marker data for the loaded and selected .cnchp file, or similar files. The Graphs tab also optionally allows the user to specifically determine the parent of origin in such genetic situations as uniparental disomy. By the user clicking on an optional button displayed in this tab, the software will display the parental information to the user. Further, the graphs tab provides the capability of clicking on various genotyping calls made by the software and various algorithms therein to run the algorithm, and display color-coded calls in a graphics window. The software disclosed herein provides the capability to a user of analyzing multiple samples simultaneously within the graphical user interface. The multi-sample karyoview allows users to view multiple patient sample data in a single screen. Each of the tabs mentioned hereinabove and following may be separated into its own separate floating window on the display screen by the user. That is, the software allows the user to click on various options using the mouse interface within the software to pull the "tabbed" information indicated above into its own new floating window.

An additional option window that may be provided may include the selected chromosome view window in the Display Area, as depicted on the right side of FIG. 9. This optional window may be used to display detected segments in selected sample files for the chromosome selected in the karyoview.

The Display Area may also optionally include and display to the user a lower pane which may include such information as, but not restricted to, the selected section of the chromosome displayed in the selected chromosome view along with detected segments and graph data in selected .cnchp files and the like, AED/BED file regions and annotations, and reference annotation files. These tracks of data may display detailed information about the genetic samples being tested, based on the differential filter settings provided by the user, and based on the use of one or more reference annotations available elsewhere to the user, such as those available generally to persons of skill in the art on-line, such as, but not limited to, the Online Mendelian Inheritance in Man (OMIM®) data library provided by Johns Hopkins University.

Further, the three views presented in the Display Area may be related. For instance, the upper pane view may simply be a macro-view of the lower pane and/or the chromosome view pane. Thus, the upper pane may be a visual representation of all possible chromosomes. When the user selects a single chromosome in the software program interface, that chromosome alone may be displayed immediately in the chromosome view pane. The user may then select in the chromosome view pane a specific region of interest, which would then be immediately displayed in the lower pane. Each pane within the Display Area may be related by orders of magnitude of data presentation, each window being a more detailed presentation of a subset of the data provided in the other panes. Adjustments or changes entered by the user into the software program for one window may immediately also effect a similar change in the other windows, such that all windows may be locked together, showing the same range of data, but in different manners.

These various display windows and user-interaction menus, described above, may be presented in many different shapes, sizes, colors and may include various additional avatars, features and/or designated markings of various shapes, sizes and colors which may be useful to the user in identifying or demarcating various CytoRegions, segments or other characteristics of the genetic data provided to the inventive software program. Though the Figures and examples or embodiments described herein are specific in certain details, it is understood by one of skill in the art that minor changes may be made in color selection, window orientation and data displayed therein, while still allowing the user to employ the differential filtering disclosed in this invention.

The Overlap Map feature of the presently disclosed software allows users to filter out common CNPs based on user BED or AED files. Reporting of all graphs and tables may be provided in combinable PDF format, which includes addition of "Interpretation" by a data analyst in each section of the Report. SNP6.cnchp files generated by GTC are viewable in the presently disclosed Affymetrix ChAS Browser, and have CN and LOH segments automatically generated.

As described above, the presently described software application allows users to define specific CytoRegions which may overlap, intersect with, or lie near segments. The presently disclosed software allows a user to apply differential filter values for areas inside the CytoRegions and additionally apply other filtering values and parameters to define data outside the CytoRegions.

Segment parameters used to filter the data, whose values are defined by the user, may include, but are not limited by, the following types of genetic features: marker count, size, and confidence. Marker count means the number of markers the segment encompasses from the start position to the end position (said start and end being defined by the software program, and the length of the segment being defined by the user). A segment typically will have at least as many markers as specified by the user to be displayed in the segment. Each marker represents a probe on the probe array, which in turn represents a sequence along the genome at a specific position in the genome. Markers are actually probe sequences of DNA on the probe array. Such probes, as defined above, may be, for instance, from about 12 to about 50 nucleotides in length. The size feature indicates the number of bases included by the user in the segment. The user, using this segment parameter interactive window, can define the minimum length of the segment to be visualized.

The differential filtering capabilities of the presently described software programs, and the depiction of these capabilities in graphical user interfaces, as described above, allows the user to visually inspect rich, complex and voluminous genetic data now made available by such genetic analysis systems as offered by, for instance, Affymetrix, Inc. of Santa Clara, Calif., such as, for instance, the Command Console system, the GENETITAN® system, the GENEATLAS® system and other such systems. Differential filtering allows the user to visualize only those aspects of the data that are pertinent to the user and to the study being performed on the experimental test samples. Thus, differential filtering is a powerful tool, providing the user with ease of manipulation of these large amounts of data, enabling a user to generate what are essentially custom-designed probe arrays within the computer software program of the invention.

While the software code that enables differential filtering may be exemplified by the following code structure, it is known to one of skill in the art that this embodiment may be altered in various manners, at various points throughout the code, and still achieve the same resultant function of enabling differential filtering. Thus, the following exemplary embodiment is offered as a non-limiting example of such code providing the differential filtering program capabilities:

```
/**Determines whether a given annotation passes through the filter.
  * @param annotation The annotation to filter.
  * @return <code>true</code> if the annotation should be passed through the filter,
  * or <code>false</code> if it should be filtered out.
  */
 @Override
 protected boolean isAnnotationPassed(final Annotation annotation) {
     if(!super.isAnnotationPassed(annotation)) {
         return false;
     }
     final CytoBrowserGenoview genoview=getGenoview( );
     final AnnotationType annotationType=annotation.getAnnotationType( ); //get the type of annotation
     final AnnotationDataCharacterization annotationDataCharacterization = annotationType.getDataCharacterization( );
     if(annotationDataCharacterization==AnnotationDataCharacterization.SEGMENTS) { //if this is a segment, see if we should filter it
         //determine the correct region (if any) the settings of which to use to filter this annotation
         final BioRegion bioRegion=genoview.getBioRegion(annotation.getBiosequence( ), annotation.getMin( ), annotation.getMax( )-annotation.getMin( ));
         //confidence
         if(isSegmentConfidenceFilteringEnabled(bioRegion, annotationType: { //if segment confidence filtering is enabled for this region and annotation type
             //if the annotation has properties, get the confidence if it is the type we expect
             final Number confidence=annotation.getPropertyValue(AED.BIO_CONFIDENCE_PROPERTY);
             if(confidence!=null && confidence.floatValue( )<getSegmentMinimumConfidence(bioRegion, annotationType))
             { //if this segment doesn't have a high enough confidence (if it has a confidence listed)
                 return false;
             }
         }
         //length
         if(isSegmentLengthFilteringEnabled(bioRegion, annotationType)) { //if segment length filtering is enabled for this region and annotation type
             if(annotation.getLength( )<getSegmentMinimumLength(bioRegion, annotationType)) { //if this segment isn't long enough
                 return false;
             }
         }
         //marker count
         if(isSegmentMarkerCountFilteringEnabled(bioRegion, annotationType)) { //if segment marker count filtering is enabled for this region and annotation type
             //if the annotation has properties, get the marker count if it is the type we expect
             final Number markerCount=annotation.getPropertyValue(AED.BIO_MARKER_COUNT_PROPERTY);
             if(markerCount!=null && markerCount.intValue( )<getSegmentMinimumMarkerCount(bioRegion, annotationType)) { //if this segment doesn't have enough markers (if it has markers)
                 return false;
             }
         }
         //overlap
         if(isSegmentOverlapFilteringEnabled(bioRegion, annotationType)) { //if segment overlap filtering is enabled for this region and annotation type
             if(genoview.getAnnotationOverlapResults(annotation).getMax.FractionalOverlapA( )>getSegmentMaximumOverlap(bioRegion, annotationType)) { //if this segment overlaps too much
                 return false;
             }
         }
         // filter based on cytoregion. This is the slowest filter, so do it last.
         if(annotationDataCharacterization==AnnotationDataCharacterization.SEGMENTS) { //if this is a segment, see if we should filter it
             if (genoview.isBlinderEnabled( ) && genoview.hideWhenBlindersAreOn(annotationType)) {
                 return genoview.overlapsACytoBioRegion(annotation);
             }
         }
```

-continued

```
    }
        return true; //this annotation passed all the tests
    }
    Likewise, the following exemplary embodiment of software code provides the software
program with the capability of determining which segment a CytoRegion may fall within:
    /**Returns the region that governs a particular range on a biosequence.
     * @param bioSequence The biosequence for which a region should be returned.
     * @param value The value on the biosequence that may be govered by the region.
     * @param extent The extent of the range on the biosequence that may be govered by
the region.
     * @return The region that governs the provided range on the given biosequence,
     * or <code>null</code> if there is no specified region for the given range.
     */
    public BioRegion getBioRegion(final BioSequence bioSequence, final int value, final
int extent) {
        readLock( ).lock( ); //get a read lock
        try {
            final Set<BioRegion>
regionSeqForSeq=bioSequenceBioRegionSetMap.get(checkNotNull(bioSequence,
"Biosequence cannot be null."));
            if(regionSeqforSeq!=null) { //if we have regions for this biosequence
                for(final BioRegion bioRegion:regionSeqForSeq) { //look at all the regions for the
biosequence
                    for(final BioSequenceSpan span : bioRegion.getSpans( )) { //look at all the spans
in this region
                        if(bioSequence.equals(span.getBiosequence( ))) { //if this span is on the correct
biosequence (just because we know this region has *some* spans on this biosequence
doesn't mean that *all* of its spans are on this biosequence)
                            if(value < span.getMax( ) && value+extent > span.getMin( )) { //if the given
span overlaps this range
                                return bioRegion; //return this first region that matches
                            }
                        }
                    }
                }
            }
            return null; //indicate that we could find no matching region for the given range
        } finally {
            readLock( ).unlock( ); //always release the read lock
        }
    }
}
```

It is to be understood that the above description is intended to be illustrative and not restrictive. Many variations of the invention will be apparent to those of skill in the art upon reviewing the above description. The scope of the invention should be determined with reference to the appended claims, along with the full scope of equivalents to which such claims are entitled. All cited references, including patent and non-patent literature, are incorporated herewith by reference in their entireties for all purposes.

What is claimed is:

1. A computer-implemented method of differentially filtering genetic data, comprising:
   accessing, by a computer comprising a processor and a memory, intensity measurement data obtained from hybridization of one or more target nucleic acid molecules to at least one of a plurality of single nucleotide polymorphism probes and a plurality of copy number variation nucleic acid probes of an array, wherein the single nucleotide polymorphism nucleic acid probes are designed to identify one or more single nucleotide polymorphisms in the target nucleic acids and the copy number variation nucleic acid probes are designed to identify one or more copy number variations in the target nucleic acids;
   converting the intensity measurement data at the processor to genetic data selectable by a user on at least one input interface window of a visual display device connected to the computer;
   displaying the genetic data on the visual display device to the user in a display area of the visual display device, wherein the display area comprises one or more user configurable windows comprising at least one of a multiple chromosomes view, a selected chromosome view, and a segment filters view;
   receiving from the user at the computer through the at least one input interface window a first set of parameters selected by the user for filtering the genetic data;
   differentially filtering at the processor, a first subset of genetic data using the first set of parameters to form a first filtered subset of the genetic data; and
   displaying on the visual display device the first filtered subset of the genetic data nearly simultaneously as the first set of parameters is received by the computer, wherein the first filtered subset of the genetic data is visualized using various colors, icons or other visual markers in the user configurable windows to distinguish from the genetic data that does not correspond to the first set of parameters.

2. The method of claim 1, wherein the view of the one or more user configurable windows comprises a genomic map, a list of single nucleotide polymorphisms, or a high-level ploidy call.

3. The method of claim 1, wherein the first subset of genetic data is selected at the computer and the input interface and is designated as one or more regions of genetic data characterized by loss of heterozygosity, long contiguous stretches of homozygosity, copy number mosaicism, or copy number variation.

4. The method according to claim 1, which further comprises:
receiving, from the user at the computer through the at least one input interface window, a second set of parameters which is distinct from the first set of parameters, wherein the second set of parameters pertains to all genetic data other than the first subset of genetic data of one or more regions of genetic data characterized by loss of heterozygosity, long contiguous stretches of homozygosity, copy number mosaicism, or copy number variation;
differentially filtering the genetic data by determining a second filtered subset of the genetic data that corresponds to the second set of parameters; and
displaying on the visual display device the second filtered subset of genetic data nearly simultaneously as the second set of parameters is received by the computer, wherein the second filtered subset of genetic data is visualized using various colors, icons or other visual markers in the user configurable windows to distinguish from the genetic data that does not correspond to the second set of parameters.

5. The method of claim 1, wherein the first set of parameters comprises at least one of a number of markers, length of genetic sequence, overlap map, or confidence value.

6. The method of claim 1, wherein the intensity measurement data is obtained from one or more labels associated with the hybridization of the target nucleic acid molecules to the nucleic acid probes of the array.

7. The method of claim 1, wherein the genetic data comprises genetic copy number data.

8. The method of claim 1, further comprising displaying, on the visual display device, the filtered subset of genetic data corresponding to the first set of parameters in multiple colors to signify different functionalities, genetic features and alleles of the genetic data.

9. The method of claim 1, wherein the visual display device comprises a visual projector, computer monitor, mobile device display, or board.

10. The method of claim 1, further comprising displaying the filtered subset of genetic data corresponding to the first set of parameters in multiple windows on a computer screen.

11. The method of claim 1, further comprising displaying the filtered subset of genetic data corresponding to the first set of parameters as a genetic map, wherein the genetic map represents a genome of a human, mouse, insect, plant or bacteria.

12. A computer program product embedded in a non-transitory computer readable medium comprising instructions executable by a processor to perform differential filtering of genetic data and interactively display the genetic data to a user, the instructions comprising:
accessing, by a computer comprising a processor and a memory, intensity measurement data obtained from hybridization of one or more target nucleic acid molecules to at least one of a plurality of single nucleotide polymorphism probes and a plurality of copy number variation nucleic acid probes of an array, wherein the single nucleotide polymorphism nucleic acid probes are designed to identify one or more single nucleotide polymorphisms in the target nucleic acids and the copy number variation nucleic acid probes are designed to identify one or more copy number variations in the target nucleic acids;
converting the intensity measurement data at the processor to genetic data selectable by a user on at least one input interface window of a visual display device connected to the computer;
displaying the genetic data on the visual display device to the user in a display area of the visual display device, wherein the display area comprises one or more user configurable windows comprising at least one of a multiple chromosomes view, a selected chromosome view, and a segment filters view;
receiving from the user at the computer through the at least one input interface window a first set of parameters selected by the user for filtering the genetic data;
differentially filtering at the processor, a first subset of genetic data using the first set of parameters to form a first filtered subset of the genetic data; and
displaying on the visual display device the first filtered subset of the genetic data nearly simultaneously as the first set of parameters is received by the computer, wherein the first filtered subset of the genetic data is visualized using various colors, icons or other visual markers in the user configurable windows to distinguish from the genetic data that does not correspond to the first set of parameters.

13. The computer program product of claim 12, the instructions further comprising displaying the first filtered subset of genetic data corresponding to the first set of parameters as a genetic map having a user interface accessible to the user, wherein the genetic map indicates different characteristics of the genetic data to the user.

14. The computer program product of claim 12, the instructions further comprising displaying the first filtered subset of genetic data corresponding to the first set of parameters as a genetic map depicted in the form of chromosomes in a window on a visual display device in a computer software network application or browser environment.

15. The computer program product of claim 12, the instructions further comprising displaying the one or more subsets of genetic data on multiple windows on a visual display device in a computer software application or browser environment, wherein each window depicts data selected by the user.

16. The computer program product of claim 12, the instructions further comprising displaying the first filtered subset of genetic data corresponding to the first set of parameters as segments of a genome on a visual display device in a computer software application or browser environment, wherein the segments of the genome comprise visual or tabular representation of genetic events.

17. The computer program product of claim 12, the instructions further comprising: displaying the first filtered subset of genetic data corresponding to the first set of parameters as a selected segment of a chromosome on a visual device display in a computer software application or browser environment, wherein the segment is selected by the user through the at least one input interface window, the segment comprising a visual or tabular representation of genetic events.

18. The computer program product of claim 12, wherein the genetic data comprises genotypes, and wherein converting the intensity measurement data at the processor to genetic data further comprises applying a dynamic modeling algorithm to the intensity measurement data by fitting values of the intensity measurement data to dynamic models and determining the genotypes by a best fit of the values of the intensity measurement data for each dynamic model.

19. The computer program product of claim 12, the instructions further comprising:

receiving, from the user at the computer through the at least one input interface window, a second set of parameters which is distinct from the first set of parameters, wherein the second set of parameters pertains to all genetic data other than the first subset of genetic data of one or more regions of genetic data characterized by loss of heterozygosity, long contiguous stretches of homozygosity, copy number mosaicism, or copy number variation;

differentially filtering the genetic data by determining a second filtered subset of the genetic data that corresponds to the second set of parameters; and displaying on the visual display device the second filtered subset of genetic data nearly simultaneously as the second set of parameters is received by the computer, wherein the second filtered subset of genetic data is visualized using various colors, icons or other visual markers in the user configurable windows to distinguish from the genetic data that does not correspond to the second set of parameters.

20. A genetic data differential filtering system, comprising:

a visual display device;

a network-enabled computer connected to the visual display device, the computer comprising:

a memory storing intensity measurement data obtained from hybridization of one or more target nucleic acid molecules to at least one of a plurality of single nucleotide polymorphism probes and a plurality of copy number variation nucleic acid probes of an array, wherein the single nucleotide polymorphism nucleic acid probes are designed to identify one or more single nucleotide polymorphisms in the target nucleic acids and the copy number variation nucleic acid probes are designed to identify one or more copy number variations in the target nucleic acids;

a processor configured to:

convert the intensity measurement data to genetic data selectable by a user on at least one input interface window of the visual display device;

display the genetic data on the visual display device to the user in a display area of the visual display device, wherein the display area comprises one or more user configurable windows comprising at least one of a multiple chromosomes view, a selected chromosome view, and a segment filters view;

receive from the user at the computer through the at least one input interface window a first set of parameters selected by the user for filtering the genetic data;

differentially filter at the processor a first subset of genetic data using the first set of parameters to form a first filtered subset of the genetic data; and display on the visual display device the first filtered subset of the genetic data nearly simultaneously as the first set of parameters is received by the computer, wherein the first filtered subset of the genetic data is visualized using various colors, icons or other visual markers in the user configurable windows to distinguish from the genetic data that does not correspond to the first set of parameters.

* * * * *